US007367675B2

(12) United States Patent
Maddalena et al.

(10) Patent No.: US 7,367,675 B2
(45) Date of Patent: May 6, 2008

(54) VISION TESTING SYSTEM

(75) Inventors: Desmond J. Maddalena, Kirrawee (AU); Simon Grbevski, Bexley (AU)

(73) Assignee: AiVision Pty Ltd., Rockdale, NSW (AU)

( * ) Notice: Subject to any disclaimer, the term of this patent is extended or adjusted under 35 U.S.C. 154(b) by 664 days.

(21) Appl. No.: 10/312,473

(22) PCT Filed: Jun. 28, 2001

(86) PCT No.: PCT/AU01/00775

§ 371 (c)(1),
(2), (4) Date: Jun. 24, 2003

(87) PCT Pub. No.: WO02/00105

PCT Pub. Date: Jan. 3, 2002

(65) Prior Publication Data

US 2004/0105073 A1    Jun. 3, 2004

(30) Foreign Application Priority Data

Jun. 28, 2000    (AU)    .................................... PQ 8428

(51) Int. Cl.
*A61B 3/02*    (2006.01)
(52) U.S. Cl. ....................... 351/237; 351/239
(58) Field of Classification Search ................ 351/237, 351/238, 239, 240, 241, 242, 243, 244, 246, 351/222, 223, 203
See application file for complete search history.

(56) References Cited

U.S. PATENT DOCUMENTS

| 3,969,020 A | 7/1976 | Lynn et al. |
| 4,105,302 A | 8/1978 | Tate |
| 5,121,981 A | 6/1992 | Waltuck et al. |
| 5,454,721 A | 10/1995 | Kuch |
| 5,477,241 A | 12/1995 | Higgins et al. |
| 5,877,841 A | 3/1999 | Jeon |
| 5,946,075 A | 8/1999 | Horn |
| 5,988,814 A | 11/1999 | Rohlfing et al. |
| 6,111,573 A | 8/2000 | McComb et al. |
| 6,238,049 B1 | 5/2001 | Griffin et al. |
| 6,364,485 B1 * | 4/2002 | Fateh .......................... 351/203 |

FOREIGN PATENT DOCUMENTS

| WO | WO 93/01744 A1 | 2/1993 |
| WO | WO 99/27842 A1 | 6/1999 |
| WO | WO 01/34020 A1 | 5/2001 |

* cited by examiner

*Primary Examiner*—Hung X. Dang
(74) *Attorney, Agent, or Firm*—Townsend and Townsend and Crew, LLP

(57) ABSTRACT

A method and apparatus are provided for testing the vision of a human subject using a series of eye tests (310). A test setup procedure (312) is run to adjust the settings of a display device (1914) such that graphic objects displayed on the device (1914) conform to a pre-defined appearance. A series of preliminary tests (314), static tests (316) and dynamic tests (318) are displayed on the device (1914), and the responses of the subject are recorded. The tests (310) may be run remotely, for example over the Internet. No lenses are required to run the tests (310).

40 Claims, 23 Drawing Sheets

VISION TESTING SYSTEM

FIELD OF THE INVENTION

The present invention relates generally to vision testing of human subjects, and in particular to the lensless testing of vision using video display screens.

BACKGROUND ART

Vision is involved intimately with almost every aspect of a person's daily life. If a person's vision deteriorates then usually so does the person's quality of life.

Vision can be divided into three conceptual layers, seen generally in FIG. 1. An optical layer 100 provides for the focusing of light onto a photosensitive layer of tissue at the back of the eye, called the retina. A functional layer 102 (formed by the retina) contains photosensitive cells which can detect various colors, motion and form, and converts these to nervous impulses which are sent to the brain. The third layer is a perceptual layer 106 which is a part of the brain that constructs a picture from the light information sent from the eyes.

During the last century, many tests have been developed to measure aspects of the vision process, and three groups of professionals: optometrists, ophthalmologists and neurologists, have had the responsibility divided among them for carrying out the tests and treating the problems involved.

Optometrists are scientifically qualified and, in general, measure and treat problems associated with the optical layer 100. As optometrists are usually the first to deal with a patient having a vision problem, optometrists often detect problems in the functional and perceptual layers 102, 106. If a pathological problem arises in area 102 or 106, optometrists generally refer patients to the professionals best qualified to treat these problems. Ophthalmologists are medically qualified and normally measure and treat problems involving both the optical layer 100 and the functional layer 102. This group of professionals will typically diagnose and treat diseases of the eye. Problems occurring in the perceptual layer 106 caused by other diseases affecting the visual process are usually referred to a neurologist. Neurologists are psychiatrically and medically qualified, and treat the problems occurring at the perceptual layer 106 when the vision process is affected by other perturbing abnormalities in the patient's brain.

It is routine for people experiencing some vision problem to visit an optometrist to have their eyes examined. The equipment used by the optometrist for examination is mainly lens-based. Since such equipment is often heavy, bulky and very sensitive, it is generally not suitable for transport. Such equipment is often quite expensive. Consequently people who lack mobility, or who live a long way from cities or large towns, have been disadvantaged through lack of optometric servicing. When optometrists do travel, generally only a small number of lenses are used for diagnostic purposes, and as such, the examination conducted may not be as thorough as one performed with the aid of the typical equipment mentioned above.

It is therefore desirable for optical examinations to be performed without reliance upon bulky, generally immobile and expensive equipment.

SUMMARY OF THE INVENTION

It is an object of the present invention to substantially overcome, or at least ameliorate, one or more disadvantages of existing arrangements.

According to a first aspect of the invention there is provided a method for testing vision of a human subject, the method comprising the steps of:

(a) adjusting at least one setting of a display device such that a sequence of graphic objects displayed on the display device conforms to a pre-defined appearance;

(b) displaying the sequence of graphic objects on the display device to test the visual functioning of the human subject;

(c) recording at least one action of the human subject performed in response to the display of the sequence of graphic objects;

(d) calculating from the recorded actions at least one aspect of the visual functioning of the subject; and (e) calculating at least one corrective lens prescription for the human subject from the at least one aspect of the visual functioning of the subject.

According to a second aspect of the invention there is provided a computer program element comprising computer program code means to make a computer execute a procedure to:

adjust at least one setting of a video display of the computer such that a sequence of graphic objects displayed on the video display conforms to a pre-defined appearance;

display the sequence of graphic objects on the video display to test the visual functioning of the human subject;

record at least one action of the human subject performed in response to the display of the sequence of graphic objects;

calculate from the recorded actions at least one aspect of the visual functioning of the subject; and calculate at least one corrective lens prescription for the human subject from the at least one aspect of the visual functioning of the subject.

According to a third aspect of the present invention there is provided a computer readable medium, having a program recorded thereon, where the program is configured to make a computer execute a procedure to:

adjust at least one setting of a video display of the computer such that a sequence of graphic objects displayed on the video display conforms to a pre-defined appearance;

display the sequence of graphic objects on the video display to test the visual functioning of the human subject;

record at least one action of the human subject performed in response to the display of the sequence of graphic objects;

calculate from the recorded actions at least one aspect of the visual functioning of the subject; and calculate at least one corrective lens prescription for the human subject from the at least one aspect of the visual functioning of the subject.

According to a fourth aspect of the present invention there is provided a system for the testing of vision in a human subject, the system comprising:

a) a server having:
  a first memory for storing an application program and one or more test results from visual testing of a human subject;
  means for receiving the one or more test results;
  means for transmitting the application program;
  means for processing the one or more test results to calculate at least one aspect of the visual functioning of the human subject; and
    means for calculating at least one corrective lens prescription for the human subject from the at least one aspect of the visual functioning of the subject; and
b) a client computer having:
  a display device for displaying a sequence of graphic objects to the human subject;

means for receiving the application program;
means for running the application program to adjust at least one setting of the display device such that the sequence of graphic objects displayed on the display device conforms to a pre-defined appearance;
means for recording the one or more test results of the human subject in response to the display of the sequence of graphic objects; and
means for transmitting the one or more test results to the server.

According to a further aspect of the present invention there is provided a method of standardizing the appearance of visual objects displayed on a video display, the method comprising the steps of:
installing an application program file on a computer;
displaying the visual objects on the video display connected to the computer;
requesting a person viewing the video display to confirm the size of at least one of the visual objects;
requesting the person to confirm whether a specified one of the visual objects is visible; and
the application program file utilizing the responses of the person to the requests to adjust the relative outputs of the colors used in displaying the visual objects and the relative dimensions of the visual objects.

According to a further aspect of the present invention there is provided a method for measuring the vision of a human subject, the method comprising the steps of:
displaying on a display device a first test to check whether the vision of the subject is within a measurement range of the method;
displaying on the display device a second test to determine a required sensitivity of the method;
selecting, based on responses of the subject to the first and second tests, further tests to display on the display device to measure an optical power of one or both eyes of the subject; wherein the further tests are selected from the group consisting of:
tests of visual acuity;
tests of spherical power;
tests of cylindrical power;
tests for astigmatism; and
tests for near visual acuity;
and wherein the subject views the first test, the second test and the further tests without lenses being interposed between the display device and the subject.

BRIEF DESCRIPTION OF THE DRAWINGS

A number of embodiments of the present invention will now be described with reference to the drawings in which:

FIGS. 15A, 15B and 15C show visual objects to be displayed on a video screen in order to test a child's visual performance.

DETAILED DESCRIPTION INCLUDING BEST MODE

Vision testing in an optometry clinic normally involves the extensive use of lenses. Disclosed herein is a vision analysis system that does not require the use of lenses. The elimination of the lenses is accomplished by a computer-based vision testing system incorporating programs which allow the vision testing to be carried out on a video display unit, such as a computer monitor, and which may be performed at a location remote from an optometrist.

Remote vision testing in this disclosure has two prime components: the vision test, and the vision diagnosis. The vision test may be performed using remote optometric equipment formed by a computer operated by the patient or an assistant. The computer is typically connected to a network such as the World Wide Web (WWW) to allow access to a further computer at which the diagnostic evaluation is undertaken.

Figure 18:
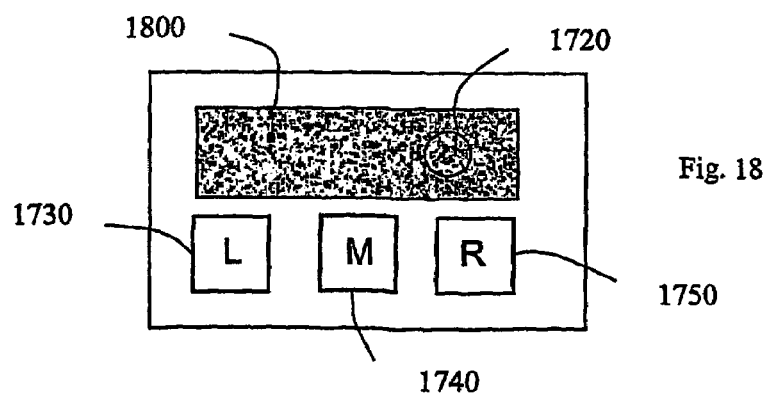
FIG. 18 shows visual objects used in the testing of stereopsis.
Figure 19:
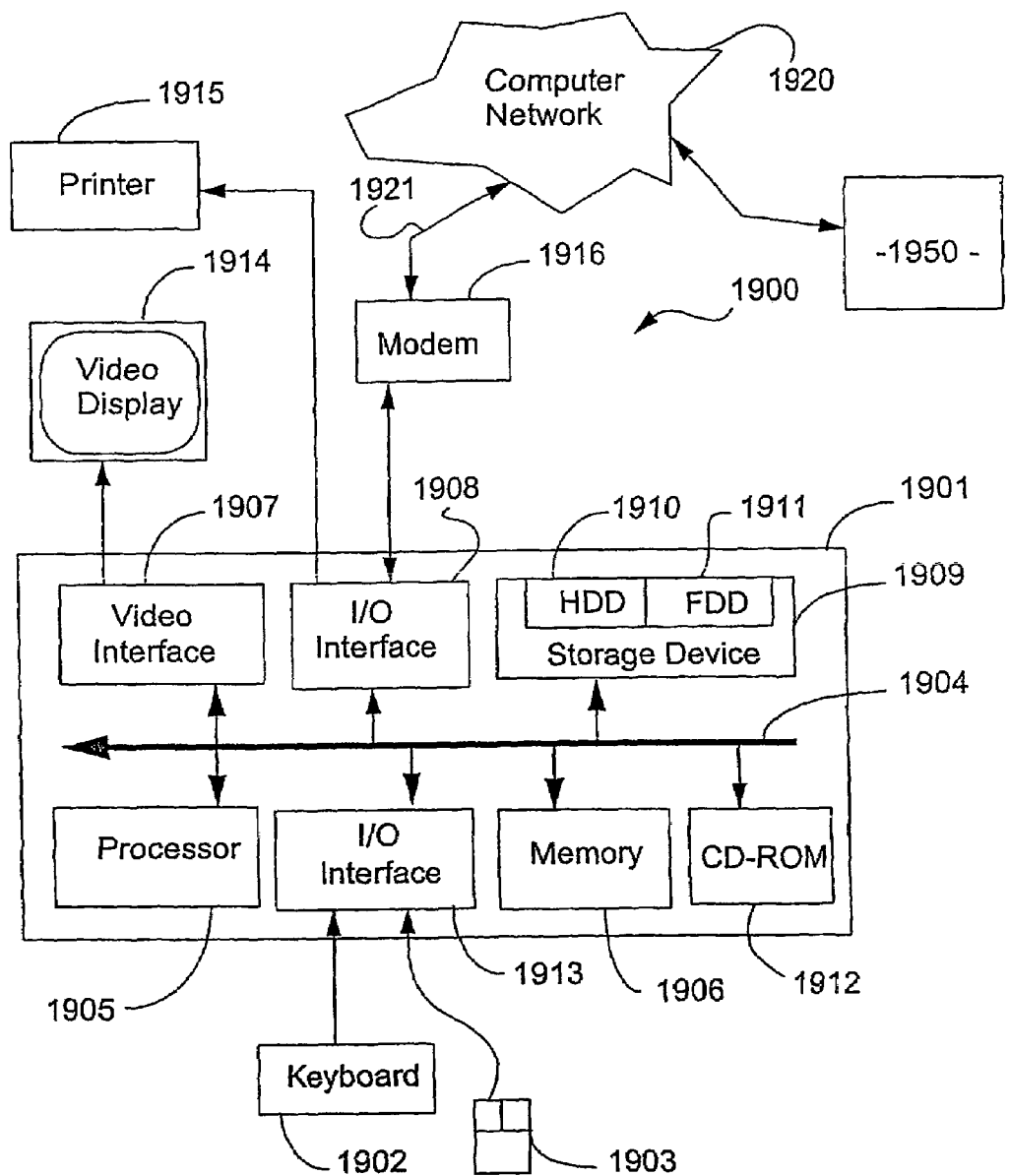
FIG. 19 shows a computer system on which the vision testing may be carried out.

The method of vision testing described herein is preferably practiced using a conventional general-purpose computer system 1900, such as that shown in FIG. 19 wherein the processes of FIGS. 2 to 18 may be implemented as software, such as an application program executing within the computer system 1900. In particular, the steps of the method of vision testing are effected by instructions in the software that are carried out by the computer. The software may be divided into two separate parts: one part for carrying out the vision testing methods; and another part to manage a user interface between the vision testing methods and the patient. The software may be stored in a computer readable medium, including the storage devices described below, for example. The software is loaded into the computer from the computer readable medium, and then executed by the computer. A computer readable medium having such software or computer program recorded on it is a computer program product. The use of the computer program product in the computer preferably effects an advantageous apparatus for vision testing in accordance with the embodiments of the invention.

The computer system 1900 comprises a computer module 1901, input devices such as a keyboard 1902 and mouse 1903 and output devices including a printer 1915 and a display device 1914. A Modulator-Demodulator (Modem) transceiver device 1916 is used by the computer module 1901 for communicating to and from a communications network 1920, for example connectable via a telephone line 1921 or other functional medium. The modem 1916 can be used to obtain access to the Internet, and other network systems, such as a Local Area Network (LAN) or a Wide Area Network (WAN).

The computer module 1901 typically includes at least one processor unit 1905, a memory unit 1906, for example formed from semiconductor random access memory (RAM) and read only memory (ROM), input/output (I/O) interfaces including a video interface 1907, an I/O interface 1913 for the keyboard 1902 and mouse 1903 and optionally a joystick or microphone (not illustrated), and an interface 1908 for the modem 1916. A storage device 1909 is provided and typically includes a hard disk drive 1910 and a floppy disk drive 1911. A magnetic tape drive (not illustrated) may also be used. A CD-ROM drive 1912 is typically provided as a non-volatile source of data. The components 1905 to 1913 of the computer module 1901 typically communicate via an interconnected bus 1904 and in a manner which results in a conventional mode of operation of the computer system 1900 known to those in the relevant art. Examples of computers on which the embodiments can be practiced include IBM-PCs and compatibles, Sun Sparcstations or alike computer systems evolved therefrom.

Typically, the application program of the preferred embodiment is resident on the hard disk drive 1910 and read and controlled in its execution by the processor 1905. Intermediate storage of the program and any data fetched from the network 1920 may be accomplished using the semiconductor memory 1906, possibly in concert with the hard disk drive 1910. In some instances, the application program may be supplied to the user encoded on a CD-ROM or floppy disk and read via the corresponding drive 1912 or 1911, or alternatively may be read by the user from the network 1920 via the modem device 1916. Still further, the software can also be loaded into the computer system 1900 from other computer readable medium including magnetic tape, a ROM or integrated circuit, a magneto-optical disk, a radio or infra-red transmission channel between the computer module 1901 and another device, a computer readable card such as a PCMCIA card, and the Internet and Intranets including email transmissions and information recorded on websites and the like. The foregoing is merely exemplary of relevant computer readable media. Other computer readable media may be practiced without departing from the scope and spirit of the invention.

The method of vision testing may alternatively be implemented in dedicated hardware such as one or more integrated circuits performing the functions or sub-functions of vision testing. Such dedicated hardware may include graphic processors, digital signal processors, or one or more microprocessors and associated memories.

Figure 1:
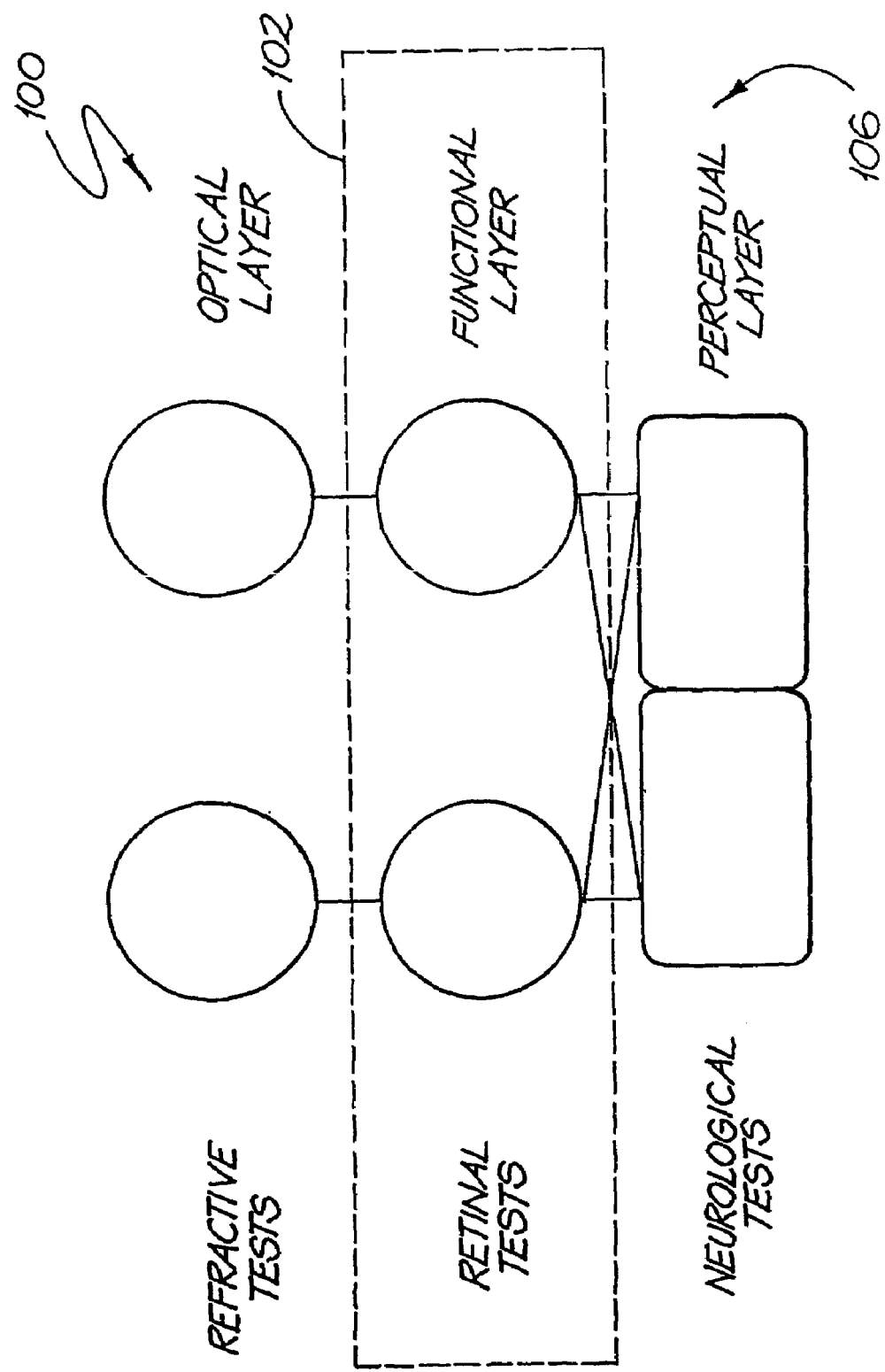
FIG. 1 shows the conceptual layers of the visual system.
Figure 2:
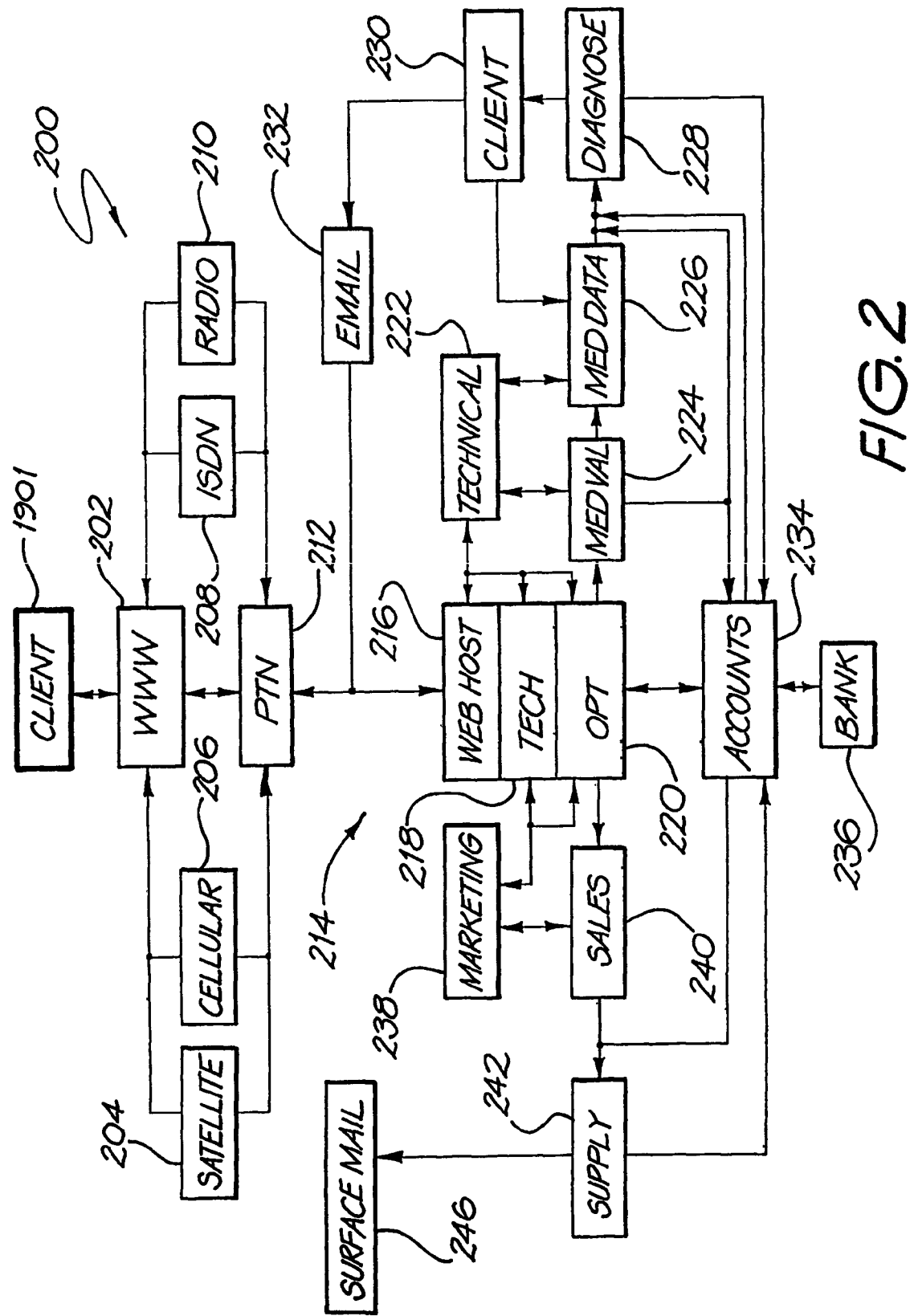
FIG. 2 shows a data flow structure illustrating how the visions tests incorporating the embodiments are distributed and analyzed.
Figure 3:
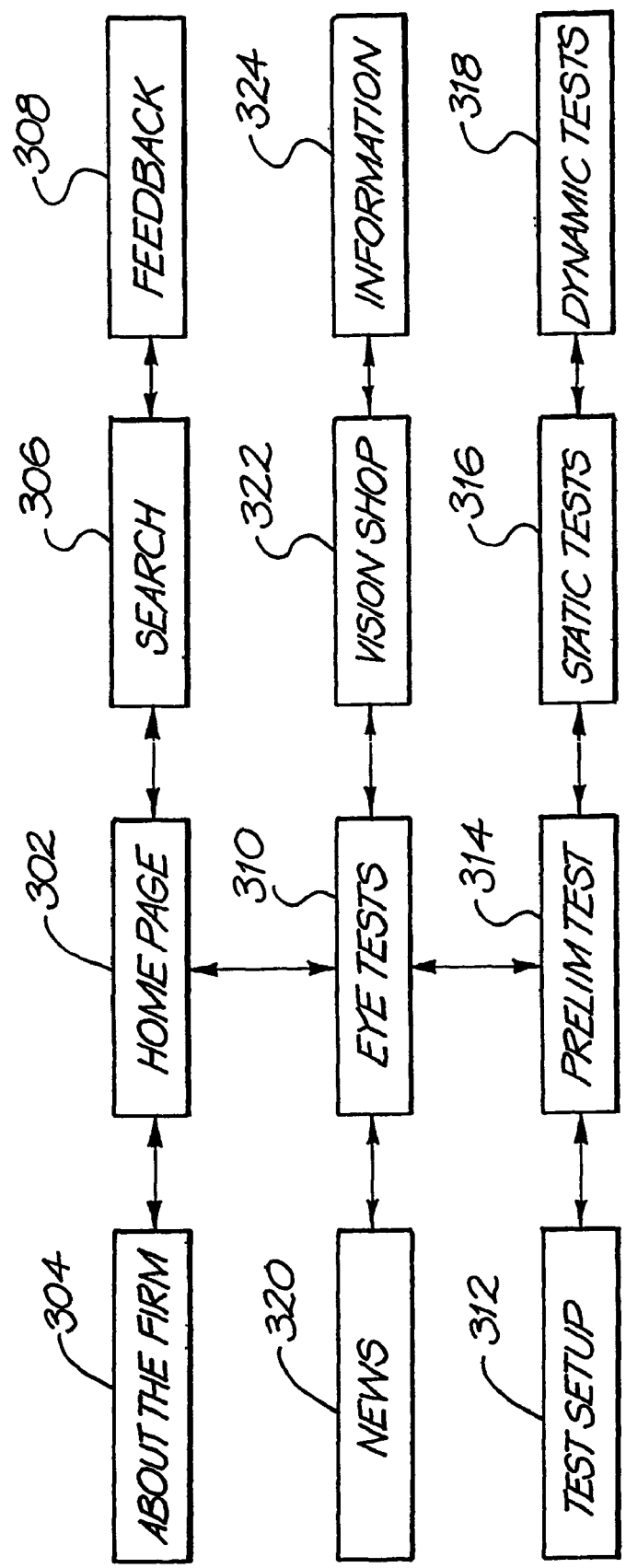
FIG. 3 shows the basic layout of an Internet web page on which the vision tests are presented.

FIG. 2 shows a network of data flow paths 200 for part of the vision testing system, typically operating from within or associated with the host computer 214, which may be formed by a server arrangement of computers. Software which enables the diagnostic evaluation to take place is stored on a component computer system 214. The computer system 214 includes a web host 216, an information management system to support the functions of a technical manager 218, and an optometry manager 220. The technical manager 218 interacts with a technical information system 222 to ensure smooth running of the system, computer maintenance, upgrades and security. The optometry manager 220 is linked to a marketing information system 238 and a sales information system 240 to relate clients' vision problems with eyewear needs. The optometry manager 220 is also linked to a clinical validation system 224, a clinical data base 226 and a diagnosis module 228 to oversee data integrity, test accuracy and authorize the release of the clinical prescription results. Prior to release of the clinical results to the client, the optometrist confirms with the accounts manager 234 that the service has been performed and that payment has been received. The accounts database 234 is in turn connected to the information system of a bank 236 or other financial institution, thus allowing the automatic processing of financial transactions with patients.

When diagnostic evaluation data is received from a patient, the data passes from the WWW 202 through a public telecommunications network (PTN) 212 to the host computer 214 where the data is passed by the optometry manager 220 for processing by the clinical validation system 224. Both the raw and the processed data are then stored in the clinical database 226. Test data from the clinical database 226 are passed to a diagnostic module 228, in which the data may either be analyzed automatically by a diagnostic assistant program 700, depicted in FIG. 7, or analyzed by a legally registered optometrist. The results of the diagnosis are then tabulated as patient/client results 230, which are then stored in the clinical database 226, and also forwarded to the patient via an email system 232 operable via the PTN 212 and WWW 202.

The marketing information system 238 is linked to a sales information system 240 which transfers information to a supply information system 242. The sales information system 240 and the supply information system 242 are both linked to the accounts database 234. Goods that are disseminated via the supply information system 242 are sent to patients by surface mail 246, either by delivery via the post office or by courier.

The PTN 212 connects to the World Wide Web 202 either directly via standard telephone lines, or alternatively by an Integrated Services Digital Network (ISDN) 208. The PTN 212 can also link to the World Wide Web 202 via a radio communication system 210, a cellular telephony system 206 or a satellite communication system 204.

A patient gains access to the vision test diagnostic evaluation system by using the computer 1901 to log-on to the World Wide Web 202 using a software application such as an Internet web browser which enables the viewing of web pages. Examples of such browsers include Internet Explorer manufactured by Microsoft Corporation and Netscape Navigator manufactured by Netscape Corporation. Using such tools, the patient is able to connect to an Internet web site 300, architecturally illustrated in FIG. 3, and operated by the web host 216 of FIG. 2. The patient will initially see a home page 302 which contains general introductory material. The home page 302 contains links to a further page 304 which contains information about the company which provides the diagnostic evaluation system. The home page 302 also provides a link to a search page 306 which allows the patient to search the web site 300 for documents containing selected words or patterns of words. If a search is initiated, the results will be displayed as a further web page 308. The home page 302 also contains a link to a web page 310 which contains more detailed introductory information about the eye tests available on the web host 216. Links are also provided to a web page 320 which describes changes to the web site 300 and gives information regarding press releases and media coverage. There is also a link to a Vision Shop web page 322 where patients are able to purchase optometric goods. The vision shop 322 has a link to an information web page 324 which contains general information about the visual system, a description of eye anatomy and eye diseases, a description of the neurology of vision, and simulated images of how the world appears to someone with vision problems.

If a patient elects to proceed with the diagnostic evaluation, the eye test web page 310 provides a link to a test set-up 312 which calibrates the video display 1914 used by the patient such that objects displayed to the patient during the testing have a standardized appearance. Once the test set-up 312 is complete, the patient may proceed to web pages which interactively perform a series of preliminary tests 314, static tests 316 and dynamic tests 318.

Figure 4:
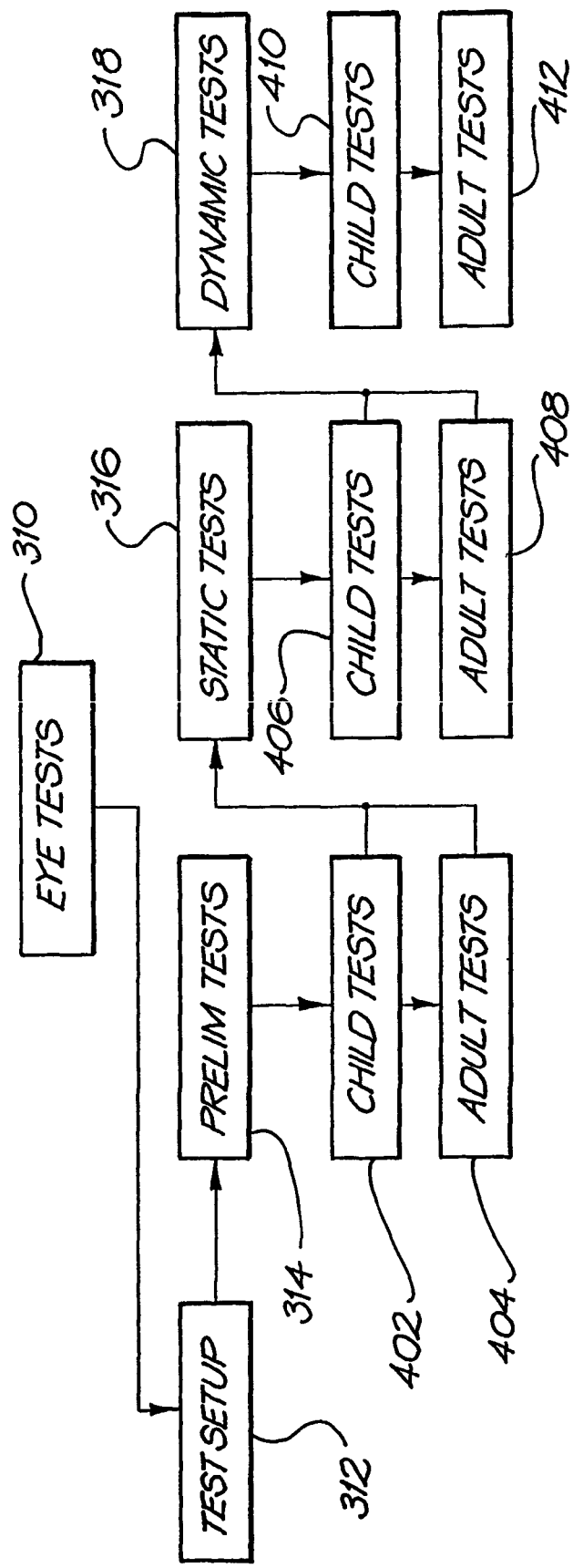
FIG. 4 shows a schematic data flow diagram illustrating the interrelationship between the vision tests.

FIG. 4 illustrates the sequence in which the eye tests 310 are performed. The test set-up 312 is a prerequisite, and performs various calibration steps. After this, a number of preliminary tests 314, static tests 316 and dynamic tests 318 are performed. Each set of tests 314, 316 and 318 may be used to assess the vision of either a child patient or an adult patient. Child tests 402, 406, 410 are desirably performed with the assistance of a supervising adult. The adult tests 404, 408 and 412 may be performed unassisted, but in general will be easier to run with the help of an assistant.

Figure 5:
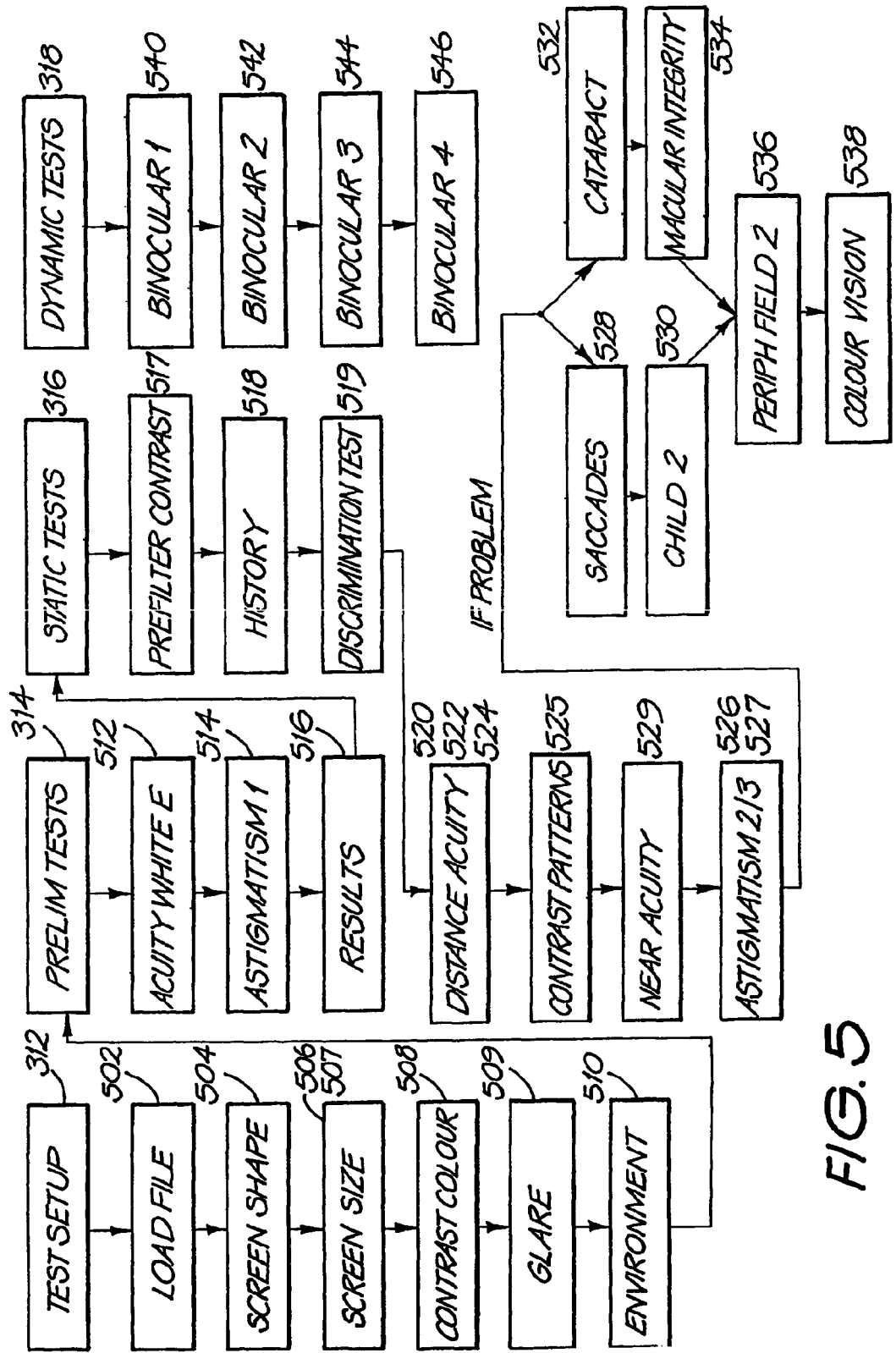
FIG. 5 shows a more detailed data flow diagram of the sequence of the vision tests.

FIG. 5 gives further detail of the eye tests 310. When the test set-up 312 is activated, there is a first load file step 502. The load file step 502 downloads a test file from the (server) computer system 214 and loads the test file into a (patient/client) computer system 1901 where the test file is stored on the hard disk drive 1910. Having completed the load file step 502, the patient is required to run a series of calibration tests to standardize the vision testing. The calibration tests include a screen shape test 504, a screen size test 506, a contrast and color test 508, a glare test 509, and an environment test 510, the latter to ensure that the lighting conditions in the room where the video display 1914 is situated will remain constant during the course of the remaining tests.

The visual tests 314, 316, 318 will be described in greater detail below, but in summary, the preliminary test 314 includes a visual acuity test 512, and an astigmatism test 514 following which a page of results 516 is presented to the patient on the video display 1914. The static tests 316 include a prefilter test 517 to determine gross pathology and refractive error status, a history questionnaire 518 concerning relevant facts of the patient's medical history, a gross visual acuity discrimination test 519, a visual acuity test 520 using a white background, a visual acuity test 522 on a red background, a visual acuity test on a green background 524, a visual acuity and pathology detection contrast pattern test 525, astigmatism tests 526 and 527, a test for the possible presence of cataracts and other diseases 532, a test 534 of macula integrity, a test of peripheral vision 536 and a test 538 of color vision. If the patient is a child there may be two further tests 528 and 530, the first to detect saccades and the second to detect visual peripheral scanning skills. Tests 532 and 534, which test for possible presence of cataracts and changes to the macula, are used only in the case where the patient is an adult. The dynamic tests 318 incorporate four tests of binocular vision 540, 542, 544, 546. Each of the above-noted tests will now be described in greater detail.

Test File Download Routine

The object of the load file step 312 is to install an application program file on the patient's computer 1901 which is configured to interact with the host computer 214, representative of the Web host 216. The application program file is in ActiveX document or Java format, or such similar computer language, to allow operation as a hypertext-aware document in an Internet browser, such as Microsoft Internet Explorer or Netscape Navigator as mentioned above.

The file contains compiled software code configured to interactively run the various tests mentioned above, including a series of tests designed to calibrate the physical characteristics of the patient's monitor 1914. The file also allows responses from the patient to be recorded for sending to the host computer 214 for analysis. During the preliminary test, the application program file calculates and displays the test results for the patient to examine. When the static 316 and dynamic 318 tests are performed, the file encrypts the results to ensure patient security, prior to the results being communicated to the host computer 1950. Some or all of the tests may be carried out on the host computer 1950 via the WWW 300 using Microsoft Active Server Page (ASP) technology rather than the patient's computer 1901. This alternative is used for example where the patient does not wish to have programs loaded onto the patient's computer 1901, where there is a need for extra security, or in cases where the tests can be more closely controlled.

Prior to the start of vision testing, it is necessary to assess the operation of the patient's computer 1901 and associated display 1914 to ensure appropriate calibration to afford a desired level of accuracy of the vision testing.

Screen Shape Test 504

Once the file is loaded on the patient's computer 1901, a page is displayed on the display 1914 to ensure that the display area of the display 1914 has been adjusted to give a rectangular image with a small straight-edged border of black around the edges. If the display 1914 cannot be adjusted to give a standard rectangular display, then a message is displayed on the display 1914 advising the patient not to continue with the tests.

Screen Size Test 506

The eye tests 310 are based largely upon the patient's responses to grey-scale and colored images of known size. Since the size of the images is likely to change with screen size and resolution, it is important to either standardize the screen size and resolution or to adjust the images displayed to be the correct size when displayed on various screen sizes and resolutions.

With typical personal computers, the screen resolution can be found by the test program directly interrogating the operating system running on the computer 1901. Examples of operating systems include Windows® manufactured by Microsoft Corporation. The actual screen size is, however, not recorded anywhere. To determine the screen size, a test has been devised in which a line of programmed length is displayed on the display 1914 by the test program, and the patient uses a ruler to measure the length of the line. The patient can then enter the measured length into the computer 1901, using the keyboard 1902 for example. Since the length of the line as seen on the display 1914 is dependent upon both the screen size and the resolution, by knowing either one of these values, the test program can calculate the other. Thus, having obtained the screen resolution from the operating system, the screen size may be readily found.

Figure 20A:
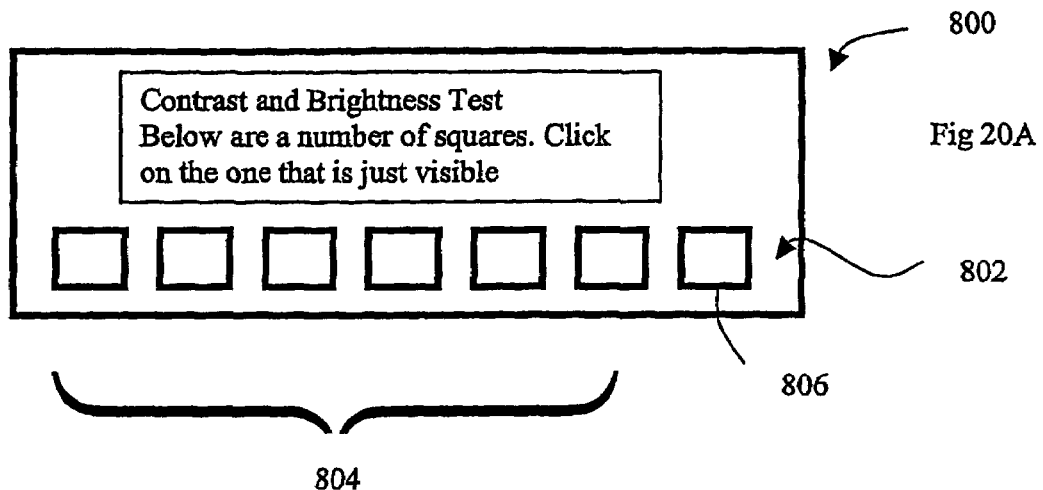
FIG. 20A shows a computer screen display for the contrast/brightness tests.
Figure 20B:
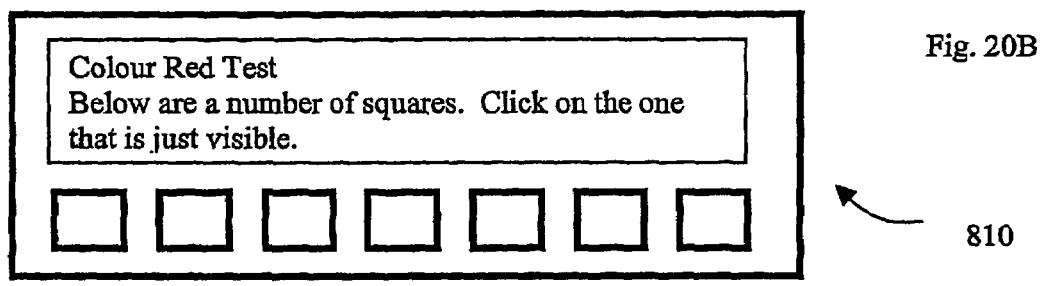
FIG. 20B shows a computer screen display for the color red test.
Figure 20C:
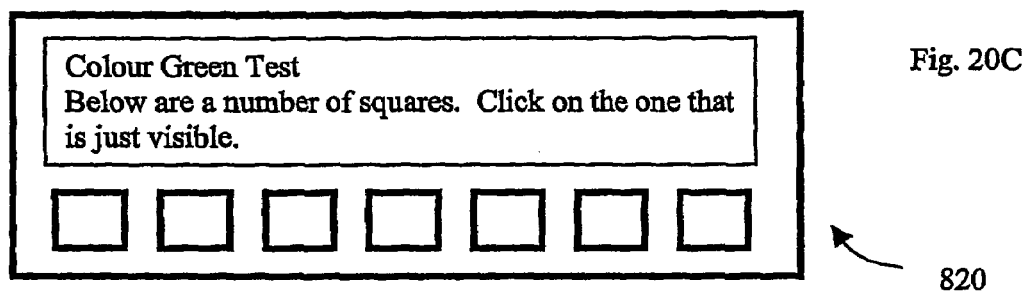
FIG. 20C shows a computer screen display for the color green test.
Figure 20D:
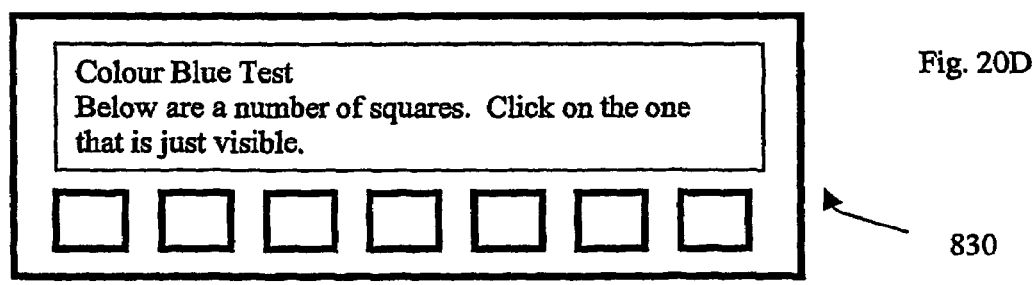
FIG. 20D shows a computer screen display for the color blue test.
Figure 20E:
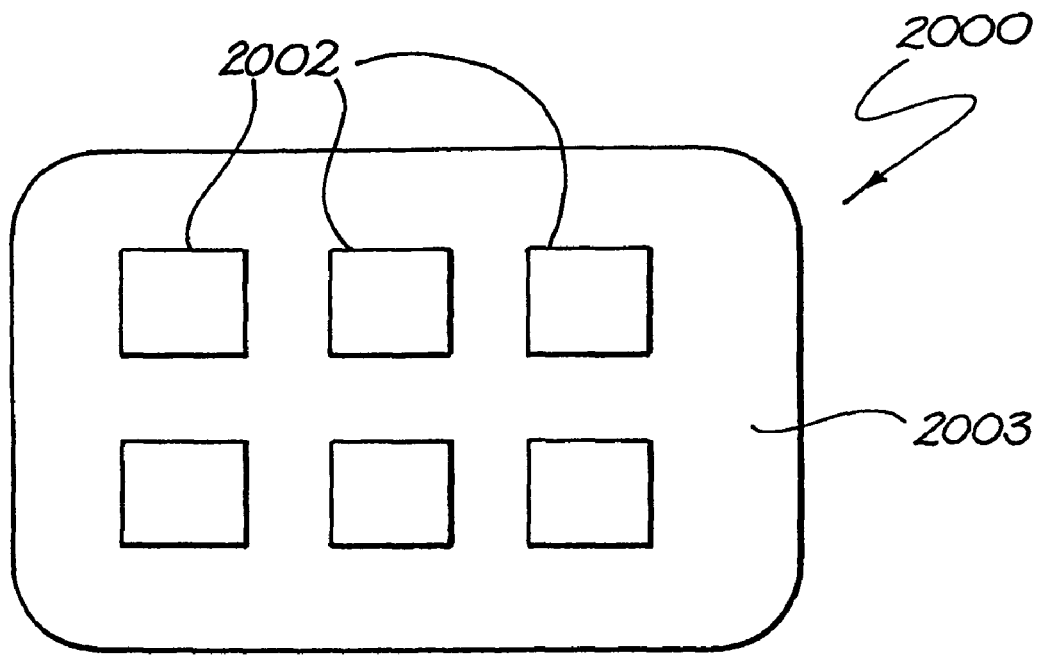
FIG. 20E shows a diagrammatic view of a computer screen display of the glare balance test.
Figure 20F:
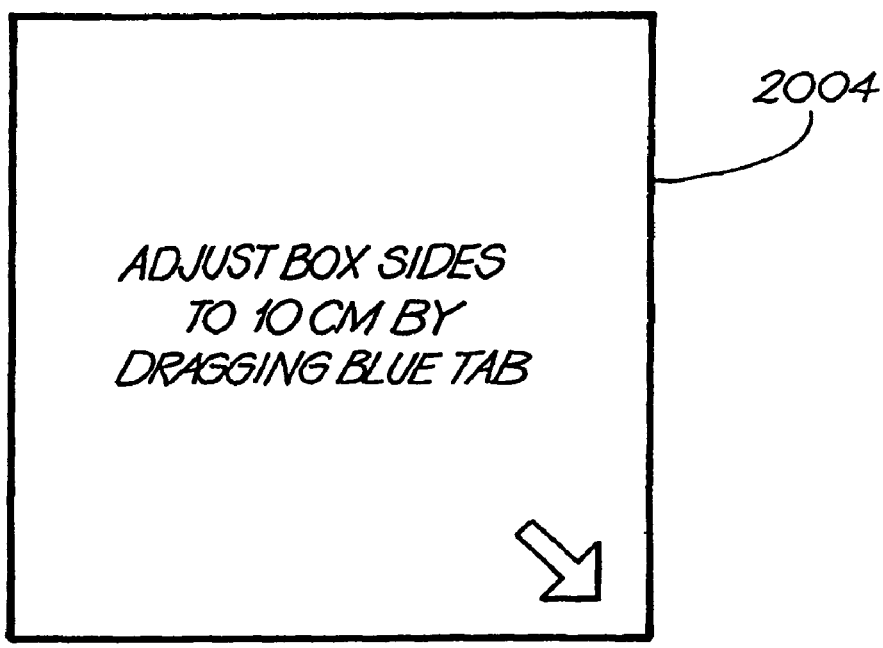
FIG. 20F shows visual objects for the size calibration test.
Figure 20G:
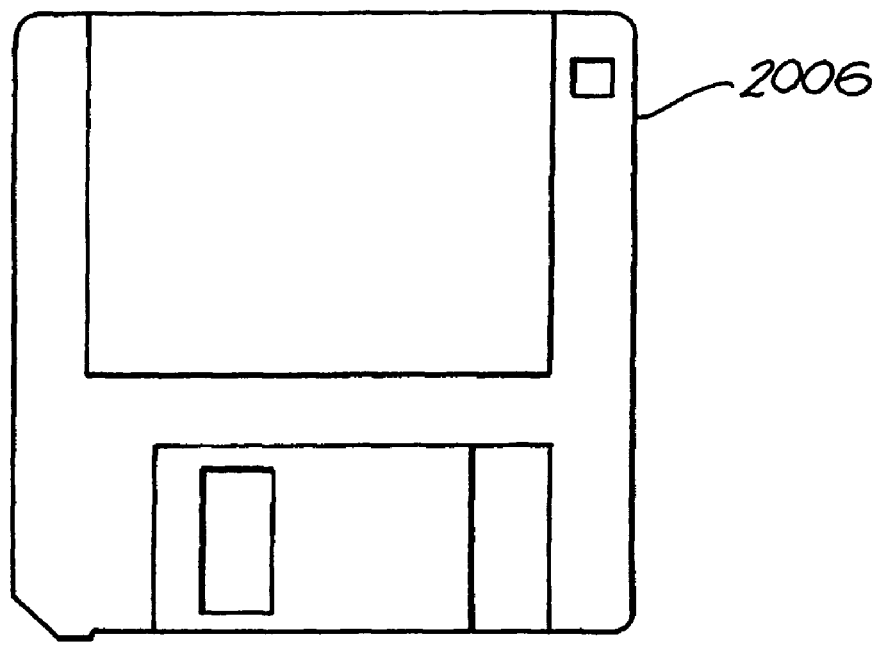
Figure 20H:
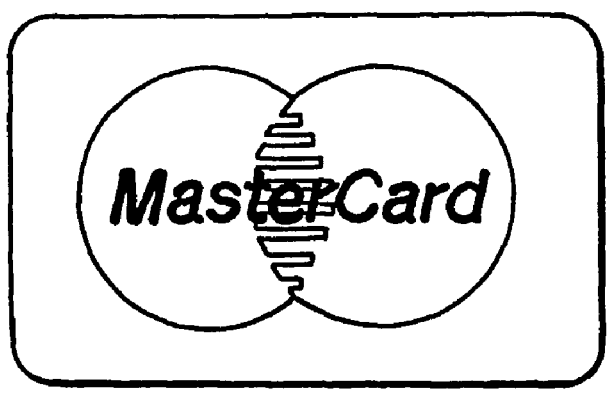

An alternative approach is to present the patient with a series of common images as shown in FIGS. 20F, 20G and 20H. These images include a square 2004 with sides of 10 cm, an image 2008 of a credit card. It is noted that the image 2008 of the credit card shows the registered trade mark "MasterCard" for illustrative purposes. Also shown is an image 2006 of a 3.5" floppy diskette. The client can then use one or more of a ruler, a real credit card or a real floppy diskette laid against the images 2004, 2006 or 2008 displayed on the computer monitor screen 1914 to measure whether the object is the same size as the object 2004-2008 on the screen. If the real object differs in size from the image 2004-2008, then the screen object is adjusted using the mouse pointer 1903 until the images 2004-2008 are the same size as the corresponding real objects. When the screen object 2004-2008 is the same size as the real objects, the screen size and resolution can be fixed.

Another approach, where the resolution is set at 800×600 pixels, is to display an image to the patient that contains lines (or other objects) of different lengths. The test program then asks the patient to use the mouse pointer 1903 to click on a line that is, or is closest to, say, 10 cm long. The line which the patient selects is then used to calculate the screen size.

Screen Contrast and Color Test 508

It is important that the display 1914 is adjusted for both black and white contrast and color to ensure that the tests which are sensitive to contrast and/or color are standardized and carried out correctly.

The screen brightness and contrast are usually adjusted by the patient, while the relative intensity of the three colors used to make up color images is usually set during manufacture of the display 1914, or by electronics repair technicians.

The contrast/brightness of the display 1914 varies according to the ambient brightness of the area (room) where the video display 1914 is located. If the area has mixtures of natural light (daylight) and artificial light, the brightness/contrast may vary considerably.

To avoid having to adjust the display 1914 throughout the day, most computer users generally have the display 1914 adjusted for the brightest part of the day, which means that the display 1914 is often too bright at other times, causing colors to be washed out, and blacks to become grey.

The contrast and color test 508 was developed to allow easy adjustment of both the contrast/brightness levels and the relative outputs of the three (red, green, blue) colors making up the color images seen on the display 1914. The test 508 provides a means of adjusting the physical parameters of the video display 1914 by using software programming to a sensitivity of less than 5%.

The contrast/brightness test is a test pattern 800 composed of seven squares 802, each having a differing grey-scale intensity ranging from pure white to black, as shown in FIG. 20A. The squares 802 are arranged from left to right on the video display 1914. The grey scales are adjusted such that on a balanced video display 1914, the left six grey-scale squares 804 should be seen, while the seventh square 806 should be invisible.

If the seventh square is still visible, then the display 1914 is too bright, and the patient is asked to reduce the brightness and/or contrast using external controls provided on the video display 1914 so as to make the seventh square 806 disappear. If less than six squares are seen, then the patient is asked to adjust the brightness/contrast controls until the left six grey-scale squares 804 can be seen.

The adjustment for the three primary colors (red, green and blue) is similar in that it uses seven colored squares varying in intensity from the full color to black. Each color (red, green and blue) is separately adjusted, in a fashion similar to FIG. 20A, as seen in FIGS. 20B-20D.

It is most often necessary to increase the intensity of one color, as the three electron guns supplying the colors do not seem to degrade at the same rates.

The color intensities are varied in a fashion that weights the faded colors more heavily than the brighter colors.

Any color adjustments can be saved in the program memory 1906 and used at a later stage to adjust images and backgrounds, to ensure that the tests use standard colors.

Screen Glare Test 509

Before eye tests 314 preferably commence, the patient is also required to measure or mark out three distances, 40 cm, 100 cm and 300 cm, from the video display 1914, as the tests 314 will be carried out with the patient's eyes positioned at predetermined distances from the video display 1914. These distances are important to ensure accuracy, as visual acuity varies with test distance.

The glare from excessive reflected light from elsewhere in the room environment may affect the ability of the patient to comfortably view the computer display 1914 and obtain optimal test results. The Screen Glare test 509 was developed to standardize room lighting, eliminate any reflected glare off the video monitor and to allow standardized adjustments of both the contrast/brightness levels and the relative outputs of the three colors (red, green, blue). The test 509 for excess glare is carried out using a visual object 2000, shown in FIG. 20E. The object 2000 consists of blue squares 2002 displayed on lighter blue background 2003. The squares 2002 are preferably 3 cm by 3 cm with an RGB value of (0, 0, 122) and the RGB value of the background 2003 is preferably (0, 0, 128). Although six squares are shown in FIG. 20E, in a typical arrangement, nine of the squares 2002 can be displayed. In this test the patient is asked to reduce the room lighting until all the blue squares 2002 are visible. Sitting at the measured distance of 300 cm, the patient is instructed to count the number of dark blue filled squares 2002 on a lighter blue background 2003. If all squares can be seen comfortably then the test is passed. If glare from some light source in the immediate environment impairs the view of any of the squares 2002, the patient is asked to adjust or block the offending light or reposition the computer display 1914 to correct the problem.

The patient is also asked to make sure that the room lighting conditions will remain unchanged during the tests.

The environment function 510 is a set of instructions relating to room lighting, glare and measuring distances from the computer display 1914.

Preliminary Tests 314

The preliminary tests 314 are of a screening nature, and involve a test for visual acuity 512 and a test for astigmatism 514. The tests 314 are carried out by the patient and analyzed by a program running on the local computer 1901 to determine whether the patient's vision is within a normal range, or whether further help is required.

Visual Acuity Test 512

The first of the visual efficiency tests is referred to as the "growing E" test and gives an indication of the functioning of the optical layer 100 and functional layer 102. The test 512 is devised to obtain an accurate measure of the visual acuity of the patient's eyes and is run in an interactive fashion over the WWW 202. A corresponding traditional test would normally be carried out in an optometry clinic by examining fixed predetermined letter sizes on a standard letter chart. The interactive test 512 is more accurate than a wall chart, as it provides a wider range of letter sizes (25 as compared with the usual nine).

Figure 9:
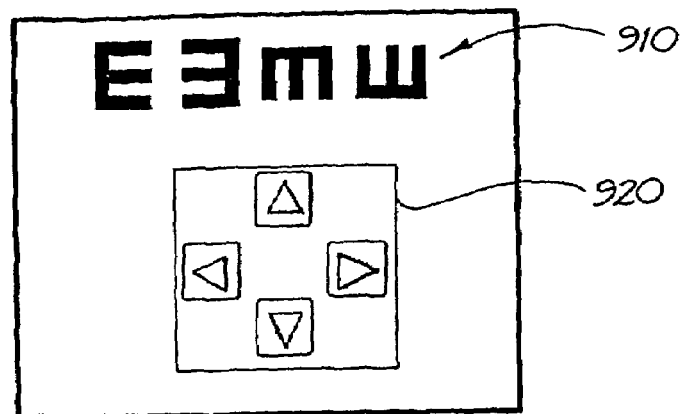
FIG. 9 shows a display used in visual acuity testing.

As seen in FIG. 9, the growing E test uses four black visual objects 910 randomly displayed on a white background, each one similar to the alphabet letter E but rotated such that each letter faces up, down, left and right respectively, the direction being determined by the gaps formed by the three arms of the letter. These visual objects 910 are referred to as E objects. Each E object is displayed in black (RGB=0, 0, 0) on a white background (RGB=255, 255, 255).

A set of written instructions is displayed on the video display 1914 indicating how the patient is to run the test 512, and how to set up the viewing distances. It is recommended that the tests should be carried out by two people, the patient and an assistant. It is also possible for the patient to do the test 512 unaided, but with a little more difficulty.

The test 512 involves the assistant starting the test 512 running by using the mouse 1903 to press a Start button icon displayed on the video display 1914. The patient watches the E object 910 grow from a small size to a very large size on the video display 1914. The size preferably ranges from 2 to 150 mm in growth increments of 2 mm. When the patient can see the direction of the gaps in the letter E, the patient asks the assistant to stop the growth of the E object 910 by clicking the mouse 1903 over a direction arrow button icon 920. If the direction is correctly named by the patient, the assistant records the result. If the response is not correct, the test is repeated until three correct responses are made. The then current size of the E object 910 is recorded.

Two controls are available to adjust the speed of the test 512. One such control adjusts the time delay interval between pressing the Start button and the start of the display of the E object 910. This is useful if a patient conducts the test without the help of an assistant, as the delay allows enough time for the patient to get into the test position before the test 512 starts. A delay of between 0.5 and 20 seconds can be selected. The second speed control allows adjustment of the object growth speed. This is the time interval between display of successive E objects 910. This is useful if the patient has poor vision, as the test 512 will reach the larger objects more quickly. The object growth speed can be varied from 0.5 to 5 seconds.

The test 512 is performed at two distances from the screen, 40 cm, and either 300 cm or 100 cm, depending upon the patient's gross visual efficiency. The testing distance is recorded for each test to indicate whether the patient's visual efficiency is measured at a normal or close distance. At each distance the test 512 is run for the left eye and the right eye individually. Each run of the test 512 is repeated three times to obtain an average object size at which the direction arrow button icon 920 was actuated. This gives a measure as to visual function for close-up tasks and for distance tasks. The size of the E object 910 viewed from a known distance is related to the visual acuity. Visual efficiency is expressed as a percentage of the visual acuity relative to the visual acuity of normal eyesight. Visual efficiency for both eyes (binocular visual efficiency) is calculated as a weighted average of the visual acuity as follows:

$$\text{Visual efficiency} = 100 \times ((3 \times (\text{visual acuity of best eye}) + (\text{visual acuity of worst eye}))/4\%.$$

First Astigmatism Test 514

Figure 10A:
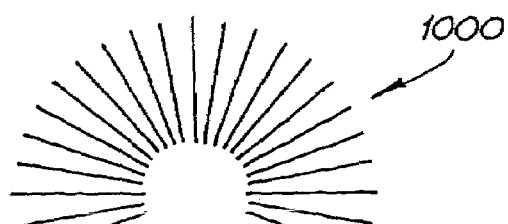
FIG. 10A shows a visual object used in testing of astigmatism.
Figure 10B:
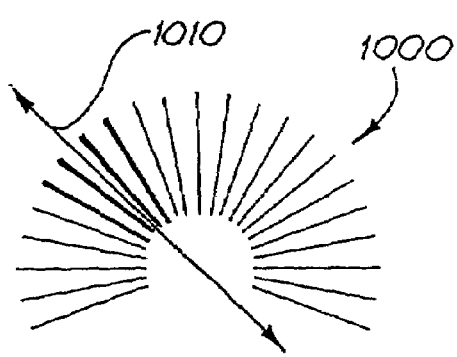
FIG. 10B illustrates the effects of astigmatism.

Astigmatism is a condition where a person's sight levels are in constant conflict for distance and near vision, with the eye reaching a point of equal blurring when neither distance nor close vision is perfectly clear. There is an irregularity to the optical surfaces of the eye that causes blurriness at all distances. The defect is similar to the distortion seen when looking through a cylindrical lens. Any lines seen through the lens that are near to parallel with the cylindrical lenses axis are seen as black, while any lines at an angle to the axis are blurred to a grey color. This is shown in FIG. 10B, where a line 1010 indicates the axis of astigmatism.

The astigmatism test 514 is designed to work in an interactive fashion with a patient over the WWW 202. The test 514 was devised to obtain a basic measure of the astigmatism of each of the patient's eyes. A corresponding traditional test would normally be carried out in the optometry clinic using a series of cylindrical lenses. The current interactive test 514 uses a black fan-shaped visual object 1000 displayed on a white background as shown in FIG. 10A.

Figure 10C:
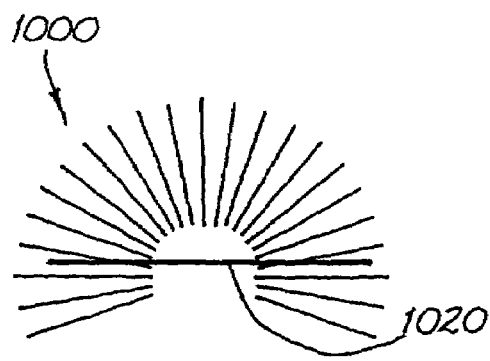
FIGS. 10C and 10D illustrate the functioning of a first astigmatism test.
Figure 10D:
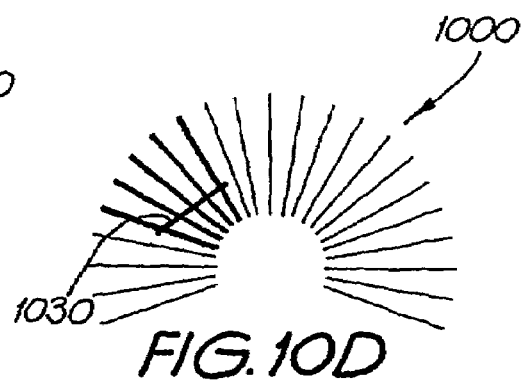

The patient uses the mouse pointer 1903 and mouse button to draw on the fan-shaped object 1000. The patient is instructed by the program to cover the left eye and to observe the center of the fan-shaped object 1000 with the right eye. If the surrounding lines are perceived to be of equal blackness, then the patient is to hold down the left mouse button and draw a horizontal red line 1020 across the image as shown in FIG. 10C. If some of the lines are perceived to be much blacker and/or thicker than the rest, then the patient is instructed to use the left mouse button to draw a red line 1030 across the blacker lines as shown in FIG. 10D. When satisfied with the line placement, the patient clicks on a displayed Record button icon using the mouse 1903, and the angular spread defined by the red lines 1020,1030 is calculated. The inverse of the angular spread in degrees is used to calculate the percentage of astigmatism. Typical levels are: mild (less than 30%), medium (30 to 60%), and significant (greater than 60%). Thus, the narrower the spread, the greater the astigmatism.

The test is repeated with the left eye open and the right eye covered.

Alternative Astigmatism Test (514)

Figure 10E:
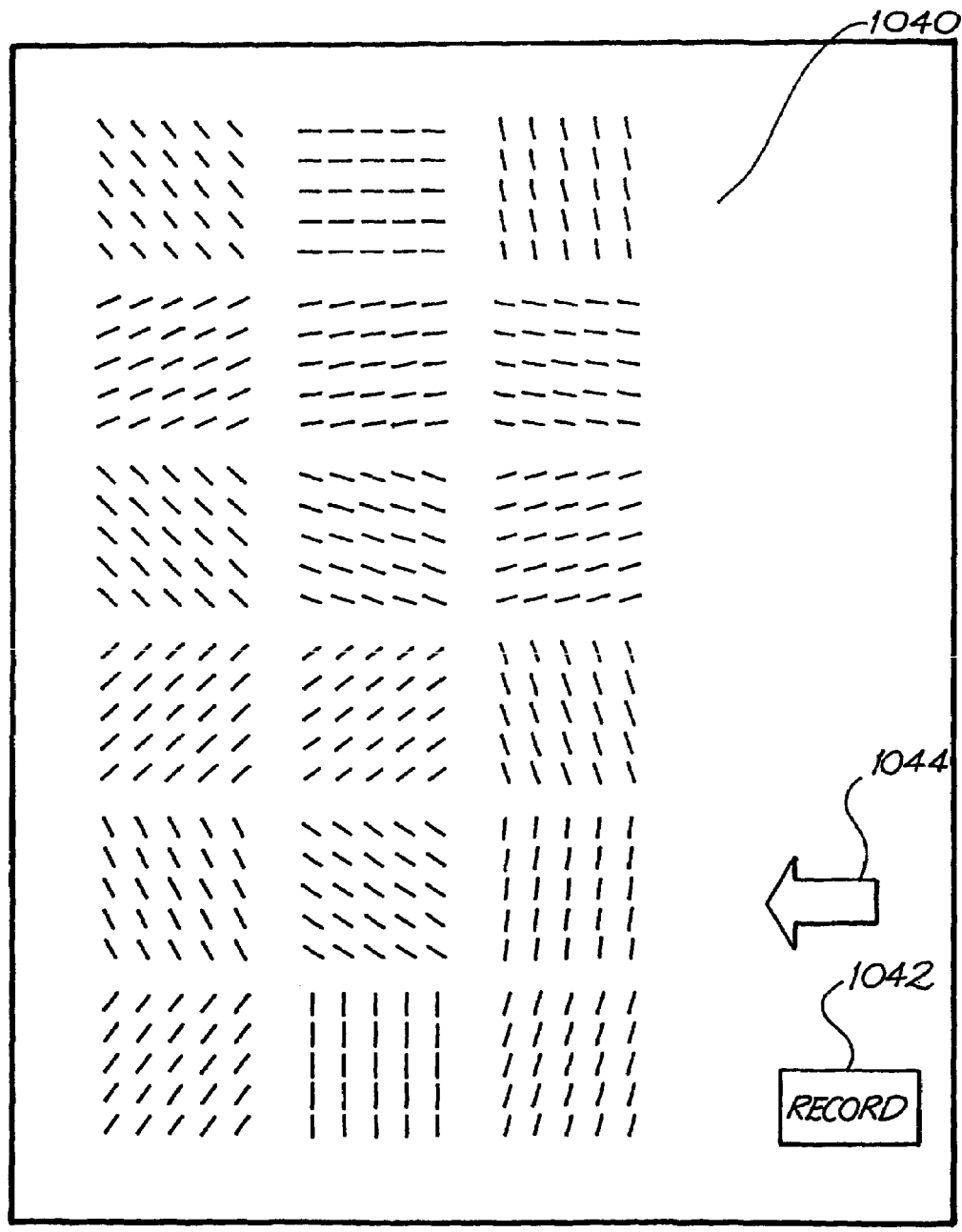
FIG. 10E illustrates the functioning of an alternative embodiment of the first astigmatism test.

In another embodiment of the first astigmatism test (514), the patient is faced with a series of 18 randomized virtual box images 1040 as shown in FIG. 10E. Each of the virtual boxes 1040 is made up of thin lines at orientations ranging from 0 to 170 degrees from the vertical. The patient is asked to cover one eye and look at the virtual box images 1040 and decide which ones are darker or blacker than the rest. The patient is asked to then point at each dark virtual box with the mouse pointer 1044 and click the left button of the mouse 1903. This will show a border around the virtual box indicating that it has been selected. If unsatisfied with any selection, the patient may click on it again to de-select it. When the patient has finished selecting the virtual boxes 1040 that are perceived to be darker, the patient is advised to press the Record button icon 1042 with the mouse pointer 1044. The angular spread as indicated by the angles of the lines making up the virtual boxes chosen is calculated.

The inverse of the angular spread in degrees is used to calculate the percentage of astigmatism. Typical levels are: mild (less than 30%), medium (30 to 60%), and significant (greater than 60%). Thus, the narrower the spread, the greater the astigmatism.

The test is repeated with the left eye open and the right eye covered.

Results of Preliminary Tests

Figure 6:
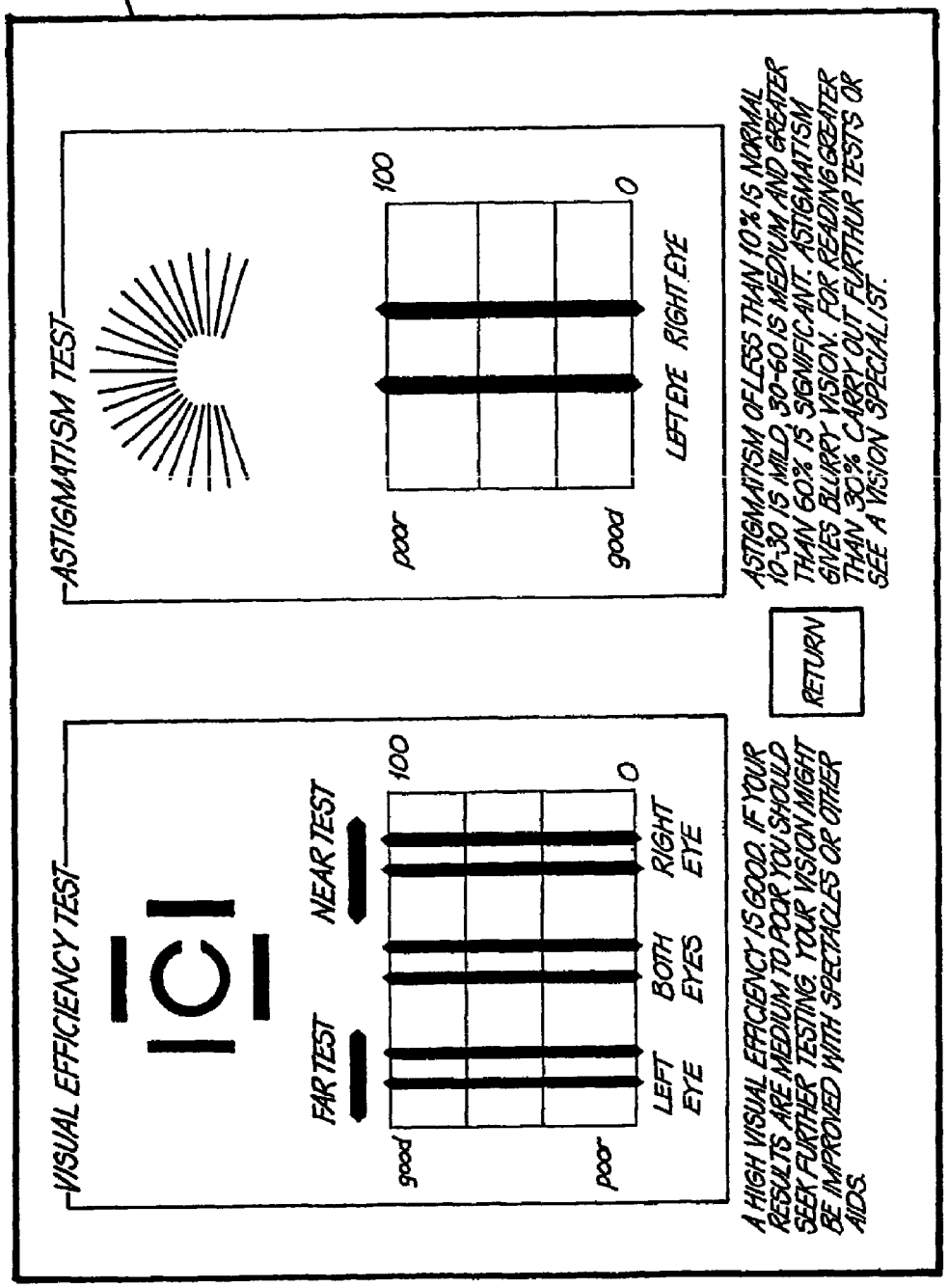
FIG. 6 shows an example of a preliminary test result as displayed on a computer screen.

The results 516 of the preliminary visual acuity test 512 and astigmatism 1 test 514 are displayed in a graphical form as shown in FIG. 6. Based upon these two tests the patient is advised whether or not to seek further help, or alternatively, that their eyes are within the normal range.

Static Tests 316

The static tests 316 are a series of tests designed to examine, in detail, several aspects of the patient's vision, including measurements of the spherical and cylindrical abnormalities of the optical system of each eye, and to also screen for some eye diseases.

An examination for cataract, macula degeneration, and glaucoma is conducted through the prefilter contrast test 517, the patient history questions 518, the macula integrity test 534 and the peripheral vision sensitivity test 536 which are carried out in adult patients. For children, many of the tests are similar to the adult tests but are adjusted for age differences in the responses. An additional set of tests including a saccades test 528 and a series of performance tests 530 using objects 1500, 1510 and 1520 shown in FIGS. 15A to 15C is used to test the child's visual skills relating to reading abilities.

In contrast to the preliminary screening tests 314, the patient does not see the results of the static test set 316. The patient is advised that the results of the individual tests will be encrypted and sent to the central optometric laboratory for examination and analysis by a legally registered optometrist.

The individual parts of the static test set 316 have been designed to work together. The patient first carries out three qualitative tests which are used to give a broad understanding of the patient's visual status and to determine which are the best quantitative tests to run to obtain optimal results. The first of the three is the prefilter contrast test 517 to give an indication of possible pathology problems and also large refractive abnormalities. This is followed by the patient history question set 518 where information about the patient's age, medical condition and vision problems is collected and scored, and finally a discrimination test 519 which uses a large stationary boxed C object 1100 shown in FIG. 11 to estimate a gross visual acuity.

Using information from the first three qualitative tests, and subsequent quantitative tests, the program uses internal logic to enable it to adjust the tests used to obtain measurements that will give the optimal results for each patient. The program follows one of several courses of action depending upon whether the patient was a child or an adult, whether there was a large or small refractive error, and whether there was pathology indicated.

For example, a near normal patient might be given the distance acuity C-test 520, the contrast pattern tests 525 and the astigmatism test 526 or 527. A child patient with reading difficulties might also be given the same tests adjusted for their age and in addition the saccades test 528 and the child performance test 530. Alternatively, an adult with a large refractive error and pathology indicated might have the test distance of the distance acuity C-test 520 and the contrast test 525 altered from 300 cm to 100 cm and be given the peripheral field test 536 and macula integrity test 534.

In the static tests 316, the visual acuity is measured using a growing boxed C object 1100, but when indicated, with red and green colored backgrounds. The use of the colored backgrounds in association with the white background allows the spherical component to be accurately estimated under some conditions.

The visual acuity is also measured, along with some signs of pathology using the contrast pattern tests 525 which use colored contrast patterns. The combination of the results from the distance acuity C-tests 520, 522, 524 and contrast tests 525 allows an accurate estimation of both spherical and cylindrical lens components.

The astigmatism 1 test 514 in the preliminary test section 312 gave a qualitative estimation of the angle of the axis and a qualitative estimate of the degree of the problems associated with the non-lens components of the optical system.

Figure 12A:
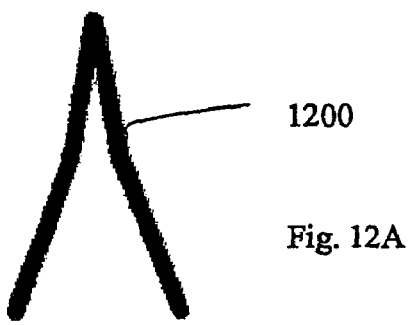
FIG. 12A shows a visual object used in assessing astigmatism.
Figure 12B:
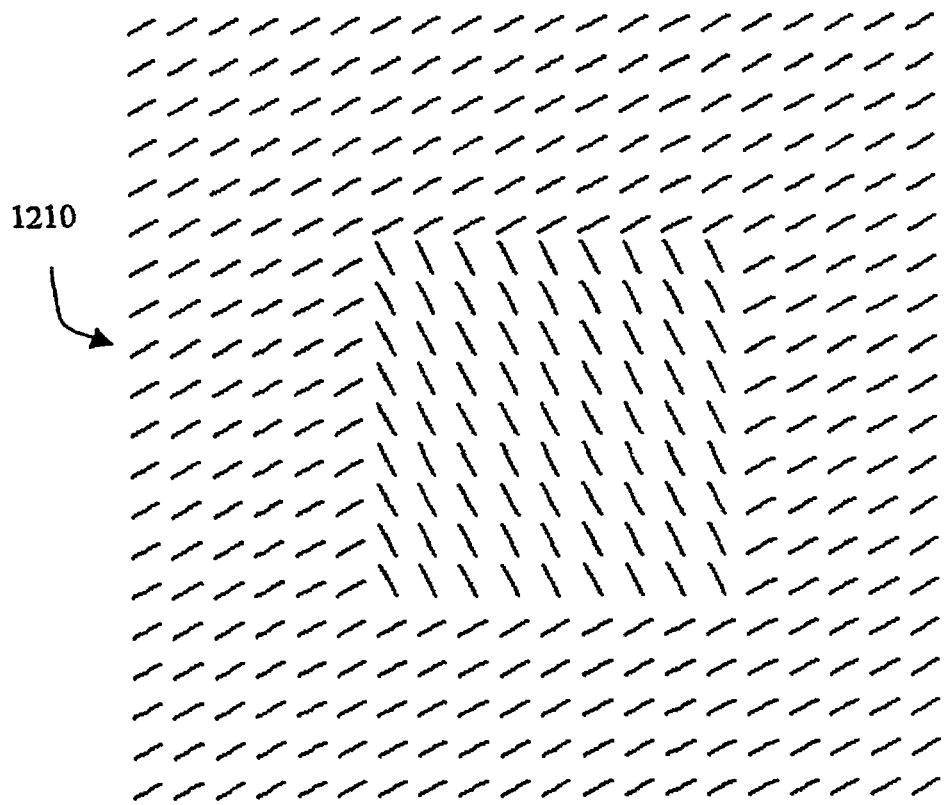
FIG. 12B shows two further objects used in the assessment of astigmatism.

In the static test section 316, the second astigmatism test 526 is measured using a new visual object 1210, as seen in FIG. 12B. This gives an accurate measurement of both the angle of the axis and the cylindrical lens power needed to correct any problems due to the astigmatism. An alternative, third astigmatism test 527 using visual objects 1225 or 1255 shown in FIGS. 12C, 12D and 12E may also be used to obtain an accurate measurement of the angle of the astigmatic axis. The astigmatism tests 526 and 527 may be used separately or together as required.

The peripheral visual field test 536 is used to examine the sensitivity of the retinal photoreceptors to both white and colored light. Reductions in sensitivity in various regions of the retina are indicative of several pathological conditions, including glaucoma, macula degeneration, diabetic retinopathy, retinopathy, optic nerve head diseases and neurological disorders such as stroke, cranial tumors, etc.

In adults, a macula degeneration test 534 is used to identify signs of deterioration of the macula, while in children a saccades test 528 is used to detect accuracy of performance of visual object refixation.

Prefilter Contrast Pattern Test 517

The test 517 was devised to obtain a qualitative assessment of the presence or absence of neurological or pathological conditions and gross refractive abnormality. The test uses an object 1265 shown in FIG. 12F and an object 1270 shown in FIG. 12G. The objects 1265, 1270 are each 8 cm square-shaped grey-scale sinusoidal contrast test patterns on a mid-grey background. The lines in the objects 1265 and 1270 are displayed both horizontally and vertically and when viewed from 300 cm will have angular frequencies of three and six cycles per angular degree. The horizontal pattern 1265 has an angular frequency of three cycles per visual angular degree and the vertical pattern 1270 is shown with an angular frequency of six cycles per visual angular degree.

The patient is given instructions on the video display 1914 and/or programmed voice instructions as to how to run the test 517, and how to set up the viewing distances. It is recommended that the test 517 be carried out by two people, the patient and an assistant. It is also possible for a single person to perform the test, but with a little more difficulty.

The test 517 involves the assistant starting the test running by selecting a Start button icon using the mouse 1903, and the patient, with one eye covered, watching the contrast patterns 1265 and 1270 while sitting at a distance of 300 cm, and directly facing the screen display.

The test 517 starts by displaying the contrast patterns 1265 and 1270 at a very low contrast (the amplitude of the sinusoidal variation in contrast is approximately 3% of full range) and the contrast is increased by the assistant selecting an icon on the display 1914 using the mouse 1903 until the patient can see the direction of the lines in the contrast patterns 1265 and 1270. At this stage the assistant presses a button on the screen display 1914 using the mouse pointer 1903 to record the result. The test is repeated with the other eye.

Normal results are indicated if the patient can see the contrast patterns at very low contrast. Medium contrast levels indicate large refractive error in the optical system and mild pathology problems. High contrast levels indicate very large refractive problems, various pathologies and neurological problems.

Patient History Questions 518

A series of questions are presented in multiple choice format on the patient's vision-related medical background and their behavior under various environmental situations and using symptomatic analysis to determine whether any vision-related problems are present. For example, patients are asked whether they can easily read the time on their watches or the fine print on the labels on a food container. Points are allocated depending on the patient's response. The allocated points are used as an indication of certain visual problems. The set of questions is designed to seek out common optometry problems and pathology. The results are scored and used along with the prefilter contrast pattern test 517 to indicate the best course of action for further tests.

To do the test 518, the patient may either sit in front of the computer and tick relevant check boxes on the video display 1914 using the mouse pointer 1903 after reading the multiple choice question themselves, or alternatively the assistant may read the questions aloud and tick the patient's reply.

Visual Acuity Discrimination Test 519

This test 519 was devised to examine for high spherical and/or cylindrical refractive error in patients. The information gained from the test 519, together with the information from the prefilter contrast test 517 and the patient's history 518, is used in deciding which are the most appropriate following tests to run to give the optimal results.

Figure 11:
FIG. 11 shows a boxed C object used in visual acuity testing.
Figure 11:

The test 519 uses a 9 cm wide black boxed C object 1100 on a white background which is placed stationary in the center of the video display screen, as shown in FIG. 11. The gap in the boxed C object may be facing in any direction. The size of the object may vary from time to time to suit local conditions.

The patient is given instructions on the video display 1914 and/or programmed voice instructions as to how to run the test, and how to set up the viewing distances. It is recommended that the test 519 be carried out by two people, the patient and an assistant. It is also possible for a single person to perform the test, but with a little more difficulty.

The test 519 involves the assistant starting the test running by selecting a Start button icon using the mouse 1903, and the patient, with one eye covered, viewing the boxed C object 1100 while sitting at a distance of 300 cm, and directly facing the screen display. The patient is asked to tell the assistant whether they can clearly see the gap in the boxed C object 1100 and which direction the gap is facing. Their answer is recorded as being able to see or not see the gap and its direction. The test is repeated for the other eye.

White Visual Acuity Test 520

The test 520 was devised to obtain an accurate measurement of the visual acuity of the patient's eyes. A corresponding traditional test would normally be carried out in the optometry clinic by examining fixed predetermined letter sizes on a standard letter chart.

The test 520 uses, also from FIG. 11, four black visual objects 1100 randomly displayed on a white background, each one similar to the alphabet letter C, but rotated such that the gap is facing up, down, left and right respectively. Each object 1100 is referred to as a boxed C object. The test 520 uses a partial border or box area around the C object to elicit the visual phenomenon known as crowding, in which letters are more difficult to identify if close to each other.

An alternative version of the test 520 uses the capital letter E in place of the letter C. The objects used would then be called boxed E objects.

The patient is given instructions on the video display 1914 and/or programmed voice instructions as to how to run the test, and how to set up the viewing distances. It is recommended that the test 520 be carried out by two people, the patient and an assistant. It is also possible for a single person to perform the test 520, but with a little more difficulty.

The test 520 involves the assistant starting the test running by selecting a Start button icon using the mouse 1903, and the patient watching the boxed C object 1100 grow from a small size to a very large size on the screen. The boxed C object 1100 size ranges from 2 to 150 mm in steps of 2 mm. When the patient can see the direction of the gap in the letter C, the patient asks the assistant to stop the growth of the boxed C object 1100 by clicking the mouse 1903 over the direction arrow icon, such as the icon 920 seen in FIG. 9.

Two controls are available to adjust the speed of the test 520. One controls the time delay interval between selecting the Start button and the start of the display of the boxed C object 1100. This is useful if a patient conducts the test alone without the use of an assistant, as it allows the patient time to get into the test position. The time delay interval can be set in the range between 0.5 and 20 seconds.

The second speed control allows adjustment of the object growth speed, which is a time interval between display of successive larger boxed C objects 1100. This is useful if the patient has poor vision as it increases the size of the boxed C objects 1100 more rapidly. The object growth speed can be varied between 0.5 and 5 seconds.

The test 520 is performed at two or three distances from the display screen 1914 depending upon the size of the refractive error, the distances being 40 cm, 100 cm and/or 300 cm. At each distance, the test 520 is run for the left eye and the right eye individually. Each run of the test 520 is repeated four times to obtain an average object size at which the direction button icon 920 was selected. This gives an idea as to visual function for close-up tasks and for more distant tasks.

Red Visual Acuity Test 522

The test 522 has been devised to obtain a more accurate measurement of the visual acuity and refractive status of the patient's eyes, when carried out in association with the white and green visual acuity tests 520, 524. Visual acuity is normally carried out in the optometry clinic by examining black letter sizes on a standard white background letter chart. The test uses the same four black visual objects 1100 used in the white visual acuity test 520, but in the present test 522 they are displayed on a red background (RGB=255, 0, 0). Once again the use of a partial border or box area around the C object elicits the visual phenomenon known as crowding where letters are more difficult to identify if close to others. The letter E may be used in place of the letter C.

The test procedure is the same as for the boxed C test in the white visual acuity test 520. The patient is given instructions on the screen and/or programmed voice instructions as to how to run the test 522 and how to set up the viewing distances. It is recommended to the patient that the test 522 is carried out by two people, the patient and an assistant, although it is possible for a single person to run the test 522.

The test 522 involves the assistant starting the test running by selecting the Start button and the patient watching the boxed C object 1100 grow from a small size to a very large size on the video display 1914. The object 1100 ranges in size from 2 to 50 mm in steps of 2 mm. When the patient can see the direction of the gap in the letter C, the patient asks the assistant to stop the growth of the boxed C object 1100 by selecting the direction arrow button 920 using the mouse 1903. As before two controls are available to adjust the speed of the test. The first controls the time delay interval between selecting the Start button and the start of the display of the boxed C object 1100. This is required if the patient conducts the test unassisted.

The second speed control allows adjustment of the object growth speed, which is a time interval between the display of successive, larger boxed C objects 1100. This is useful if the patient has poor vision, as it increases the rate at which the boxed C object 1100 grows to a large size, thus reducing the waiting period.

The test 522 is performed at two or three distances from the screen depending upon the size of the refractive error, 40 cm, 100 cm and/or 300 cm. At each distance the test 522 is run for the left eye and the right eye individually. Each run of the test 522 is repeated four times to get an average object size at which the Stop button was selected. The size of the boxed C object 1100 viewed from a known distance is related to the visual acuity with corrections for red colored light. Using different background colors tests different components of the visual process. In particular a red background is used in identifying far-sightedness.

Green Visual Acuity Test 524

The test 524 is carried out in conjunction with the white and red visual acuity tests 520, 522 in order to obtain a more accurate measure of the visual acuity and refractive status of the patient's eyes. Visual acuity is normally carried out in the optometry clinic by examining black letter sizes on a standard white background letter chart. The test uses the same four black visual objects 1100, the boxed C objects, that were used in the white and red visual acuity tests 520, 522. In this case the boxed C objects 1100 (RGB=0, 0, 0) are displayed on a green background (RGB=0, 210, 0). As described before, the partial border around the C object elicits the visual phenomenon known as crowding. The letter E may be used in place of the letter C.

The test procedure is the same as was used in the white and red visual acuity tests 520, 522. As before it is recommended that the test 524 is carried out by two people, the patient and an assistant, although the patient may run the test 524 alone using the time delay interval controller and the object growth speed controller. The results of the test relate to visual acuity with corrections for green colored light. The green background helps in the identification of short-sightedness.

Contrast Pattern Test 525

The test 525 was devised to give an accurate measure of visual acuity and an indication of certain underlying pathology conditions.

Figure 12C:
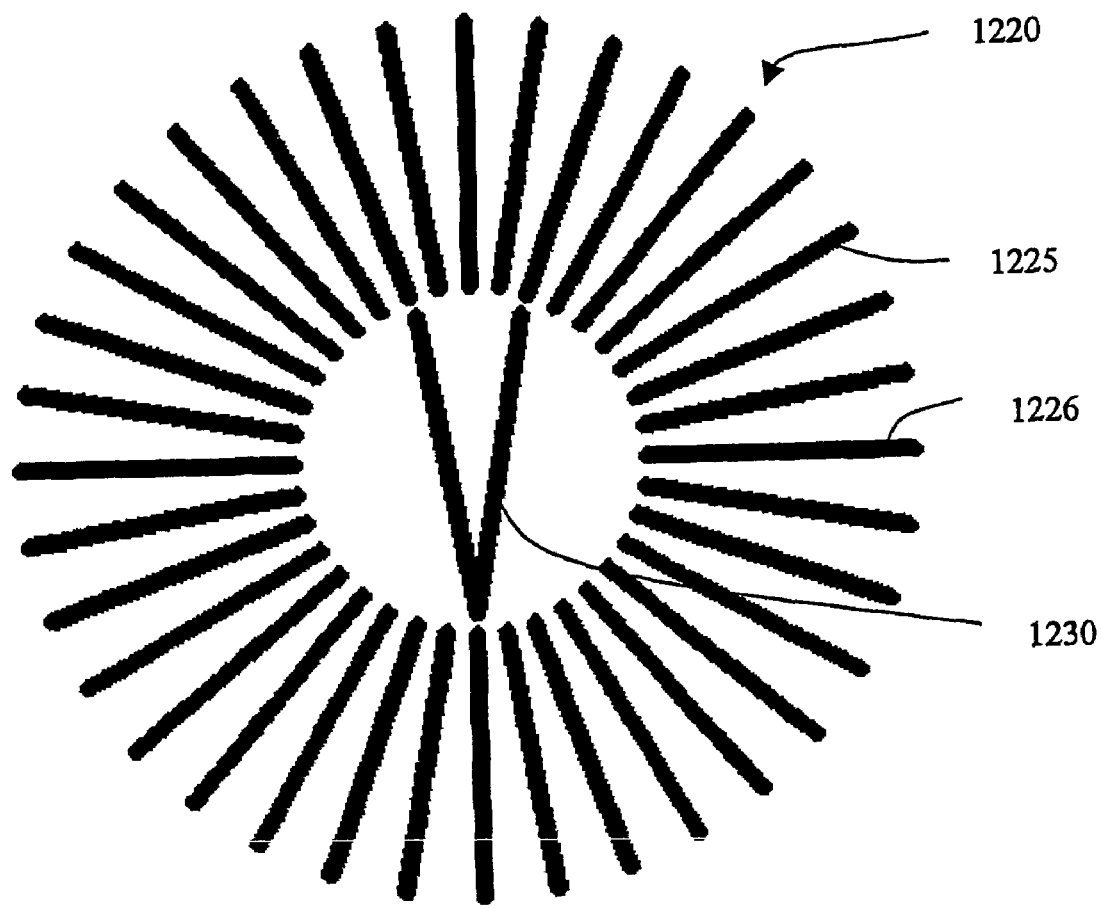
FIG. 12C shows alternative objects used in the assessment for astigmatism.
Figure 12D:
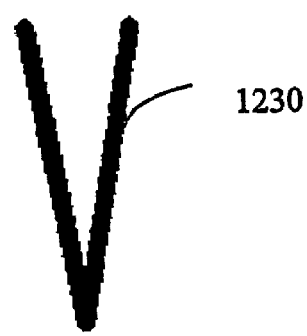
FIG. 12D shows alternative objects used in the assessment for astigmatism.
Figure 12E:
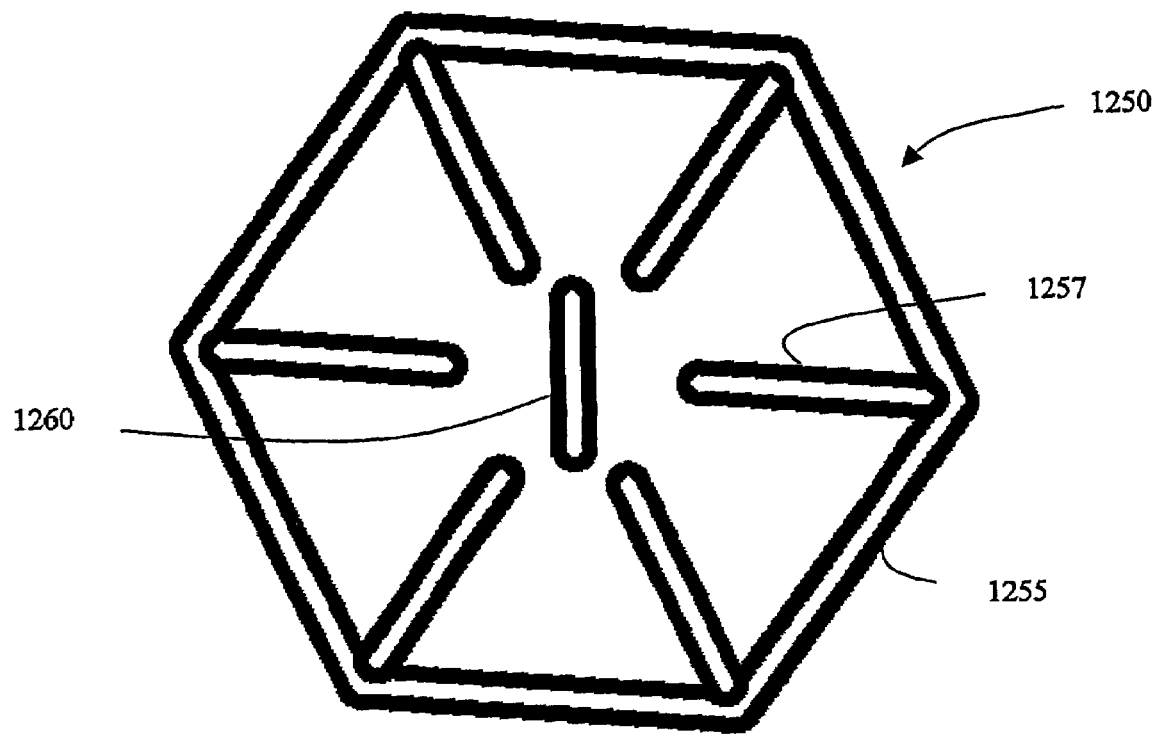
FIG. 12E shows alternative objects used in the assessment for astigmatism.
Figure 12F:
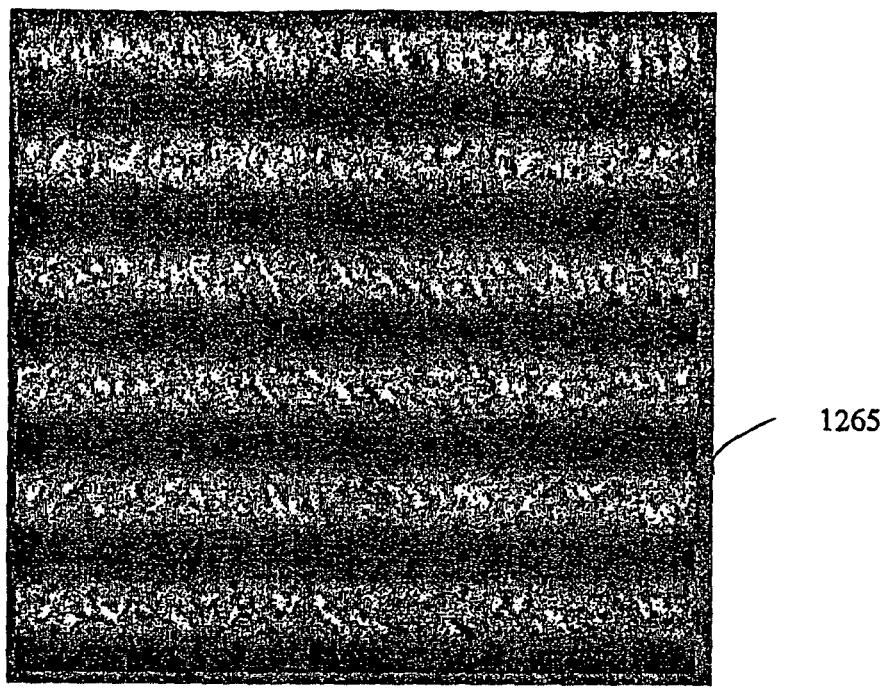
FIGS. 12F and 12G show two example patterns used in testing gross visual acuity.
Figure 12G:
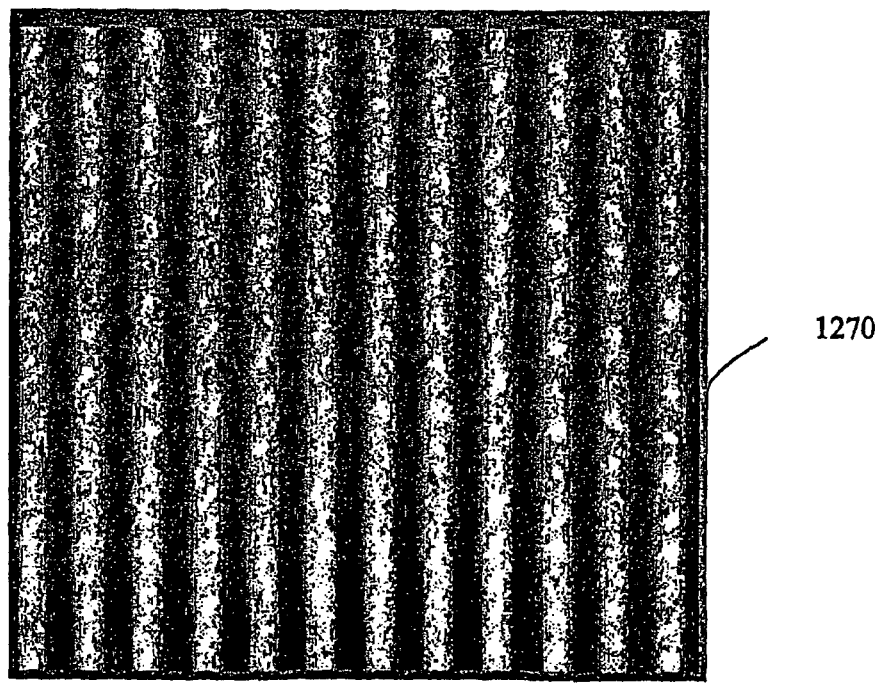
Figure 12H:
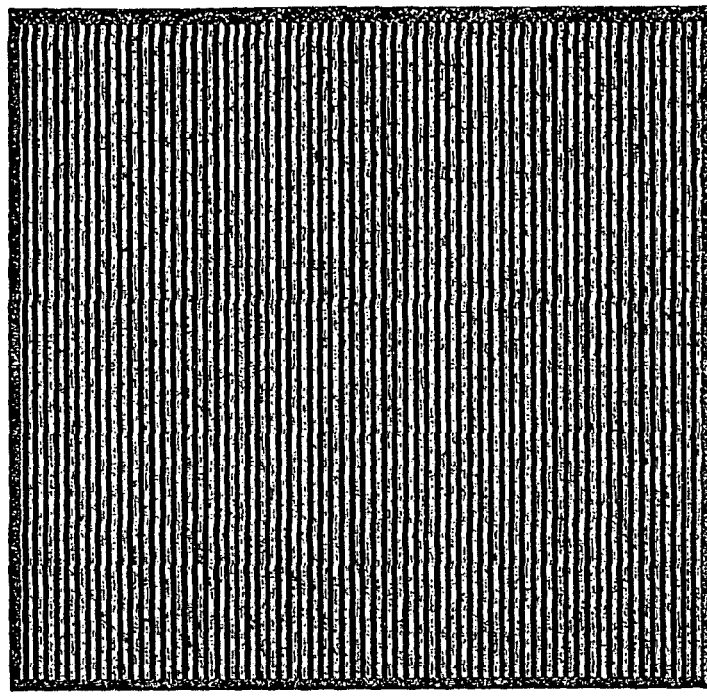
FIGS. 12H, 12I and 12J show three example patterns used in testing visual acuity.
Figure 12I:
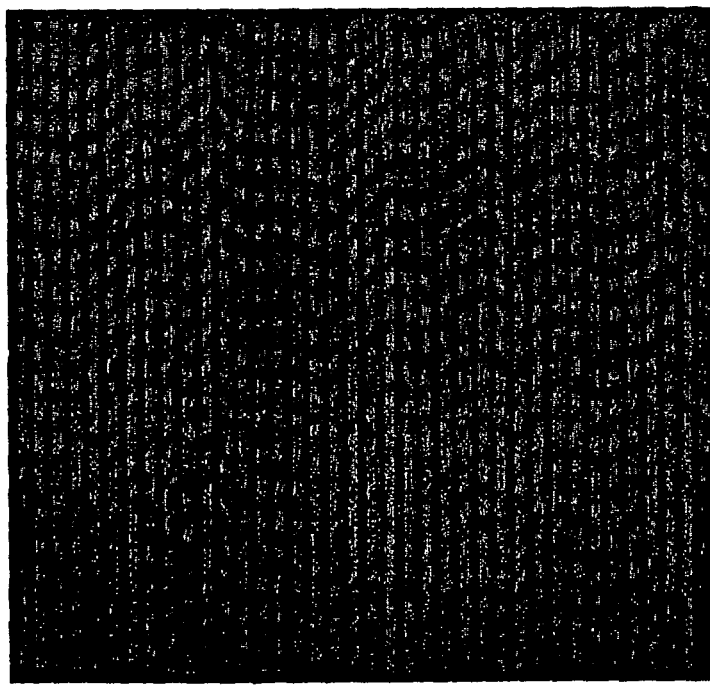
Figure 12J:
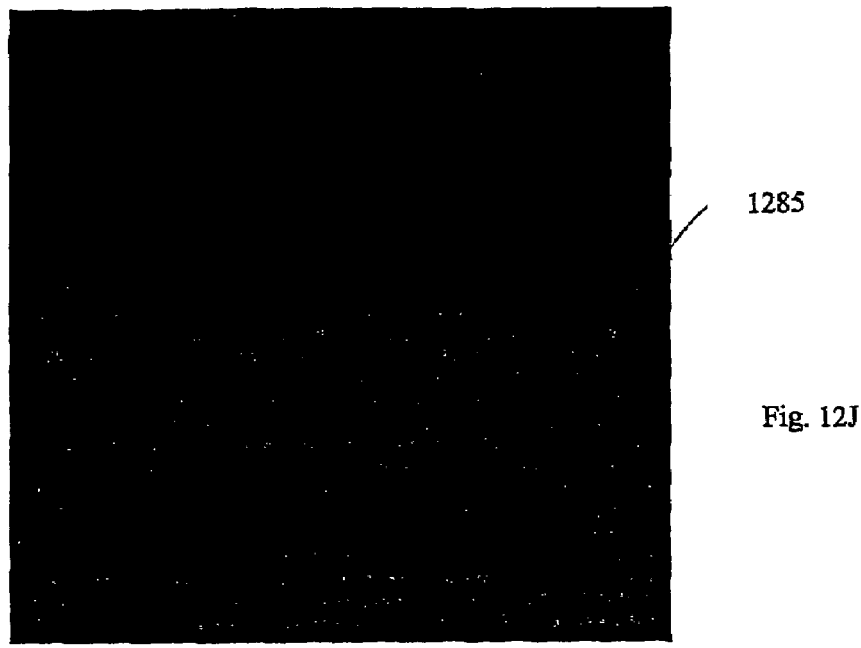
Figure 12K:
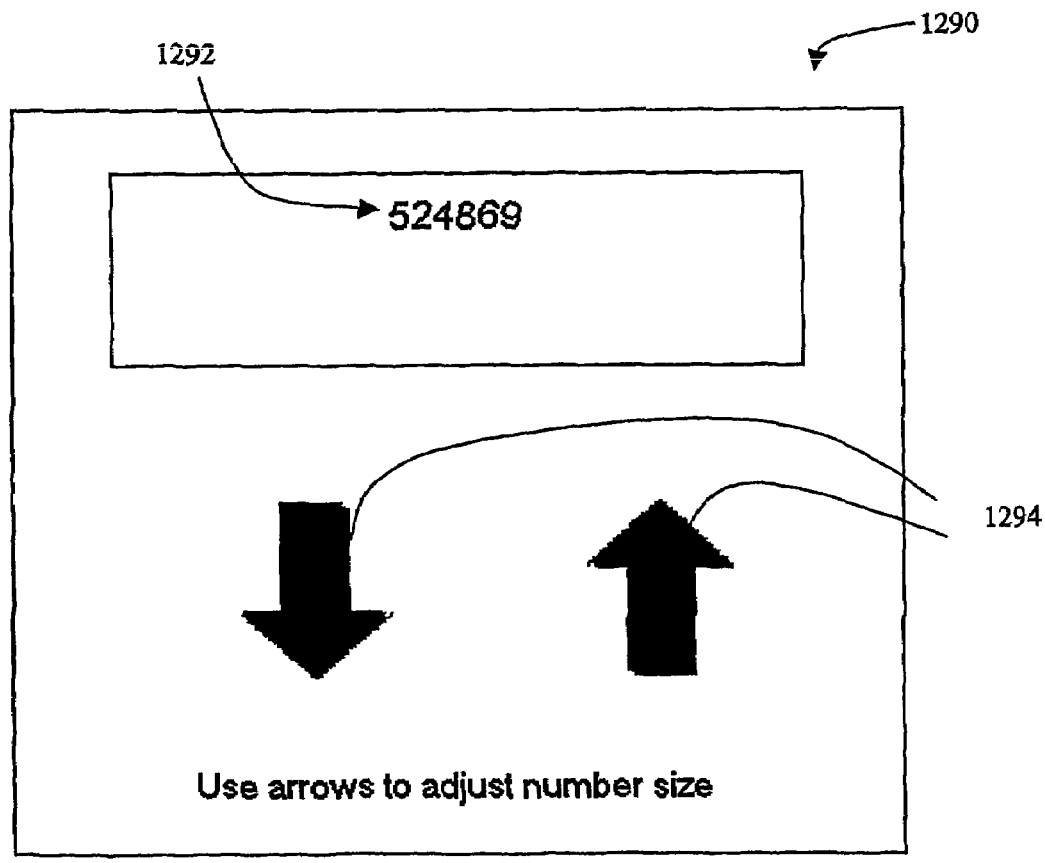
FIG. 12K shows a test window used for testing near visual acuity.

The test uses objects 1275, 1280 and 1285 shown in FIGS. 12H and 12J. The objects 1275, 1280 and 1285 are sinusoidally varied contrast test patterns displayed in 8 cm squares. Object 1275 is a grey-scale pattern with a vertical pattern of 36 cycles per visual angle when viewed from 300 cm, object 1280 is a red-scale vertical pattern of 24 cycles per visual angle and object 1285 is an example of a blue-scale pattern showing horizontal lines at 12 visual cycles per visual angular degree. The patterns in objects 1275, 1280 and 1285 may be rendered obscure by poor reproduction of darkly shaded images.

The lines in the patterns 1275, 1280 and 1285 are typically displayed in both horizontal and vertical orientations, but may be also displayed at other angles, and when viewed from 100 cm or 300 cm will have angular frequencies from three to 36 cycles per angular degree. The amplitude of the sinusoidal variation in contrast is set to 50% of full range.

The patient is given instructions on the video display 1914 and/or programmed voice instructions as to how to run the test, and how to set up the viewing distances. It is recommended that the test 525 be carried out by two people, the patient and an assistant. It is also possible for a single person to perform the test, but with a little more difficulty.

The test 525 involves the assistant starting the test running by selecting a Start button icon using the mouse 1903, and the patient with one eye covered watching the contrast patterns 1275, 1280, 1285 while sitting at a distance of 100 cm or 300 cm, and directly facing the screen display.

The contrast patterns 1275, 1280, 1285 having the highest frequency, 36 cycles per degree, are displayed first and then patterns with decreasing frequency are displayed until the patient can see the direction of the lines in the test pattern. At this stage the assistant selects a button on the screen display 1914 using the mouse pointer 1903 to record the result. The tests are performed for grey, red and blue contrast patterns. The test is repeated for the other eye.

The pattern of results for the grey, red and blue contrast patterns when measured at 100 cm or 300 cm or both can be related to both the magnitude of the spherical and cylindrical refractive components of a corrective spectacle prescription.

Contrast C Test 532

One of the problems with optometric tests is that they may give incorrect answers when the patient is suffering from some visual disorder. Several disorders, including astigmatism, cataracts, macula degeneration and pituitary tumors, may cause a reduction of sensitivity to visual images.

A contrast test 532 is provided, which in cross-reference with the other tests indicates potential problems resulting from these disorders.

The test 532 uses a very light-grey growing boxed C object (RGB=240, 240, 240) on a white background (RGB=255, 255, 255). This boxed C object has a very low contrast to the white background but has the same shape as the objects 1100 discussed earlier. The boxed C object normally detects mild to severe astigmatism, and will give an indication of problems associated with several disorders depending on the severity of the disorder. The procedure of the test 532 is identical to that of the white, red and green visual acuity tests 520, 522, 524. The results of this contrast test 532 are used in conjunction with the white, red and green acuity tests 520, 522, 524. A poor result in the contrast test 532 indicates the possible presence of visual disorders, and the patient is advised to seek further examination from an optometrist or ophthalmologist.

Second Astigmatism Test (Virtual Box Astigmatism Test) 526

The preliminary tests 314 provided to the patient included a first astigmatism test 514, and a brief description of the condition was provided in the discussion of the first astigmatism test 514.

The second astigmatism test 526 forms part of the static testing 316, and makes use of a contrast graded arrowhead-shaped visual object 1200 which is displayed on a white background as shown in FIG. 12A. The arrowhead object 1200 is rotated through 180 degrees during the test 526, in intervals of 1 degree.

The test 526 uses a virtual box image 1210 composed of two unbound box forms, one smaller, the inner virtual box, that is located inside a larger virtual box. Each virtual box is made up of short parallel lines oriented by the user. The lines inside the smaller inner virtual box are perpendicular in orientation to those in the outer virtual box.

The test program allows the patient to accurately determine the angle of the astigmatic axis by the differential grey shading of the sides of the arrowhead object. A slider bar is provided on the video display 1914, and the arrowhead object 1200 can be rotated by using the mouse 1903 to move the slider bar. The patient is instructed to rotate the arrowhead object 1200 until both its sides are perceived to be of equal blackness. The patient then selects a Record icon to store the axis of astigmatism, which is determined by the arrow direction. The axis will be different for each eye, and if the patient does not have much astigmatism, the arrowhead object 1200 will look substantially the same at all angles.

The next part of the test 526 carries out a measurement of the astigmatic power range, which is determined by the difference between the near focal range and the far focal range. The virtual boxes 1210 shown in FIG. 12B are displayed on the video display 1914 with the line orientation of the inner virtual box in the same orientation as determined by the arrowhead object 1200 in the first part of test 526. The patient is instructed to state whether the inner smaller virtual box appears to stand out from the larger virtual outer box or the outer virtual box appears to stand out from the inner smaller box. The patient is asked to move towards or away from the video display 1914 until the-two sets of virtual boxes appear to have equal blackness, darkness or thickness. It is then necessary to measure the distance from the eye to the video display 1914.

The result is typed into a box on the video display 1914 and the Record icon is selected using the mouse 1903 to store the information.

The patient is then instructed to move towards or away from the video display 1914 until the inner smaller virtual box of the object 1210 appears to be blacker, darker or thicker than the outer larger virtual box of the object 1210. Once again the distance from eye to video display 1914 is measured, and the result is entered into a box on the video display 1914 and the Record button is selected.

As the final step of this test 526, the patient is instructed to move towards or away from the video display 1914 until the larger outer virtual box of the object 1210 appears to be blacker, darker or thicker than the inner smaller virtual box of the object 1210. As before the distance between the eye and the video display 1914 is measured, and the result is entered into a box on the video display 1914 and the Record button is selected using the mouse 1903. The lines on the virtual boxes can also be substituted with colored lines and the test repeated in the same manner.

The astigmatic power is determined by the difference between the near focal range and the far focal range. These latter ranges are calculated using the distance measurements taken during the test 526.

The Third Astigmatism Test (Windmill Test) 527

In the second astigmatism test using the virtual box test 526, the axis of astigmatism is found using a rotating arrowhead. The windmill test 527 provides an alternative test that under some conditions proves to be more sensitive and more readily acceptable to many patients.

The windmill test 527 uses an object 1220 shown in FIG. 12C composed of a series of lines (e.g. 1225, 1226) having a thickness which may be varied. Lines 1225, 1226 are radially distributed as an annulus around a center region containing a V-shaped arrowhead object 1230, which is also shown in FIG. 12D and which can be rotated through 360 degrees. When the test is running, the radial lines 1225, 1226 are rotated clockwise around the center like the vanes of a windmill. The speed of rotation is adjustable from 1 to 20 angular degrees per second and the thickness of the lines 1225, 1226 is adjustable from 1 pixel to 20 pixels.

The rotation of the radial lines 1225, 1226 draws the attention of the viewer with astigmatism to the fact that those of the lines 1225, 1226 lying in the axis of astigmatism are seen to be darker than others. The V-shaped arrow 1230 can then be rotated to point to the center of the axis of astigmatism. When near the center of the axis, the equal darkness of the two sides of the V-shaped arrowhead 1230 can be used for fine tuning in a similar manner as with the arrowhead object 1200 used in the second astigmatism test 526.

The ability to vary the thickness of the lines 1225, 1226 during rotation of the radial lines helps patients with various degrees of astigmatism to adjust the line thickness to an optimal thickness for their individual vision problem.

When the patient has considerable blur owing to a large spherical refractive problem in addition to the astigmatism, the radial line object 1220 shown in FIG. 12C becomes less effective. Under these conditions an alternative hexagonal object 1250, shown in FIG. 12E, may be used instead of the radial line object 1220. The object 1250 consists of an outer hexagonal shape 1255. From each vertex of the hexagon 1255, a line 1257 projects towards the center of the hexagon 1255. The lines 1257 do not reach the center of the hexagon 1255 but leave a central clear region. A line 1260 is positioned in the clear central region and may be moved independently of the hexagon object 1255. The central line 1260 is used with the hexagonal figure 1255 to align to the angle of astigmatism.

When the test is running, the hexagonal part 1255 of object 1250 shown in FIG. 12E is rotated clockwise around the center. The speed of rotation is adjustable from 1 to 20 angular degrees per second and the thickness of the lines 1257 is adjustable from 1 pixel to 20 pixels.

The rotation of the hexagonal object 1250 draws the attention of the patient with astigmatism to the fact that the divisions and sides of the hexagon 1250 lying on the axis of astigmatism are darker than the remaining divisions and sides. The central line 1260 shown in the object 1250 can then be rotated to align with the hexagonal dividing lines 1257 that appear darkest and match the axis of astigmatism which is parallel to the angle of the darkest sides. When nearing the alignment to the darkest of the dividing lines the central line 1260 will appear continuous and bolder.

The patient is given instructions on the video display 1914 and/or programmed voice instructions as to how to run the test, and how to set up the viewing distances. It is recommended that the test 527 be carried out by two people, the patient and an assistant. It is also possible for a single person to perform the test, but with a little more difficulty.

The test 527 involves the assistant starting the test running by selecting a Start button icon using the mouse 1903, and the patient with one eye covered watching the rotating radial line figure 1220 or hexagonal figure 1250 while sitting at a distance of 100 cm, and directly facing the screen display.

The end point of the test 527 is recorded by the assistant selecting a Record button using the mouse pointer 1903 when the arrowhead object 1230 of the radial line object 1220 or the center line 1260 of the hexagon object 1250 is indicating the axis of astigmatism. The test 527 is repeated for the other eye.

Near Visual Acuity Test 529

The test 529 was devised to give an accurate measure of visual acuity at near distances. The test uses a small box-shaped window 1290 shown in FIG. 12K in which is displayed a series of six to eight randomly generated numerals 1292. In the example shown in FIG. 12H the random number 1292 is "524869". The numerals 1292 start off at the beginning of the test at the screen resolution which is approximately 5 point on a screen operating at a resolution of 800×600 pixels, but may be smaller on higher resolution screens. The numerals 1292 increase in size by whole points at the selection of an arrow 1294 activated by the mouse pointer 1903. The object of the test 529 is to measure the smallest point size of the numerals 1292 that the patient can see. The numerals 1292 are generated randomly so that the patient cannot guess them. The point size of the numerals 1292 is used to determine an estimate of the near visual acuity.

The patient is given instructions on the video display 1914 and/or programmed voice instructions as to how to run the test, and how to set up the viewing distances. It is recommended that the test 529 be carried out by two people, the patient and an assistant. It is also possible for a single person to perform the test, but with a little more difficulty.

The test 529 involves the assistant starting the test running by selecting a Start button icon using the mouse 1903, and the patient with one eye covered watching the number box 1290 while sitting at a distance of 40 cm, and directly facing the screen display.

The end point of the test is reached when the patient can read aloud the sequence of numerals 1292 displayed on the screen without error. This point is recorded by the assistant selecting a Record button using the mouse pointer 1903.

The test 529 is repeated with the other eye.

First Peripheral Field Test 536

A number of pathological disorders are known to cause a reduction of sensitivity or loss of photoreceptive function in the retina of the eye. The peripheral field test 536 is designed to map the sensitivity of the photo receptors.

If the patient normally wears visual aids such as glasses or contact lenses they should be used during the test.

Figure 13:
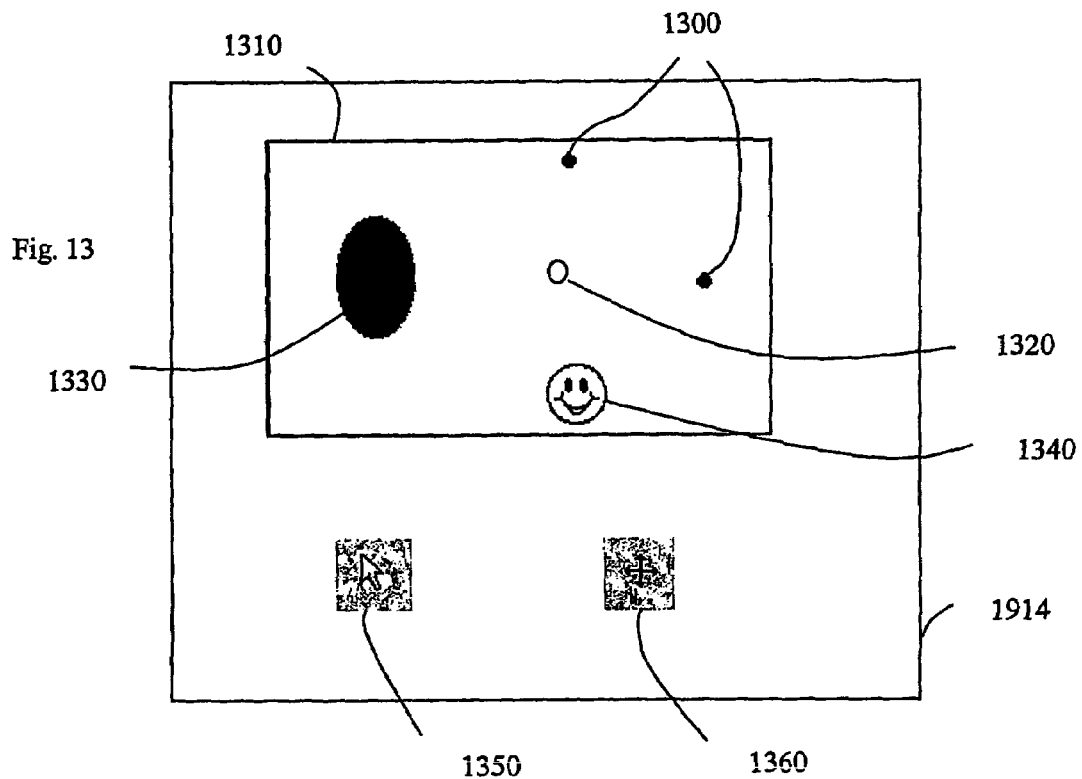
FIG. 13 shows visual objects used in assessing peripheral vision.

The test 536 as seen in FIG. 13 presents spots 1330 which are light grey to white in color on a mid-grey background screen 1310 for a short interval of time. The patient tracks a moving target object 1320 on the video display 1914 using the mouse pointer icon 1350, and when a spot 1300 appears the patient is instructed to press a button on the mouse 1903 to record the sighting.

When a spot 1300 is sighted the position of the spot 1300 is recorded, allowing a map of photoreceptor sensitivity to be drawn. Loss of sensitivity in various regions of the retina is indicative of different types of visual disorder.

A typical screen used in the peripheral field test 536 is shown in FIG. 13. The patient is instructed to cover his or her left eye with a patch, and then to move his or her face to a position 25 cm from the video display 1914. In order to support the patient's head and help maintain it at the correct distance and height from the video display 1914, the patient is instructed to rest his or her elbow on a table and to rest his or her chin in the left hand.

The patient is then instructed to fixate on the central "orange circle" target object 1320. While fixating on this target object 1320, the patient is to adjust his or her distance from the video display 1914 by rocking backwards or forwards on his or her elbow until the black oval 1330 on the right side disappears into the eye's blind spot. The patient's eyes should also be at the same height as the orange circle target object 1320.

The patient then moves the mouse pointer icon 1350 into the middle of the target object 1320 using the mouse 1903. A soon as the arrow 1350 is in the correct position overlapping the target object 1320, the mouse pointer icon 1350 will change into a multidirectional icon 1360. The goal is then to keep the multidirectional arrow 1360 steady inside the target object 1320 at all times as the target object 1320 moves around on the video display 1914. Test results are only recorded while the multidirectional arrow 1360 is maintained inside the target object 1320. Intermittently, while the patient is moving the multidirectional arrow 1360 inside the moving target object, a grey spot will flash somewhere in the patient's peripheral vision. Each time a spot 1300 is perceived in peripheral vision, the patient clicks on the left mouse button. This process is repeated each time a spot 1300 is seen flashing somewhere on the video display 1914. Each time the patient currently observes a spot 1300, a smiley-face object 1340 is displayed on the video monitor 1914.

The procedure is then repeated for the left eye.

To increase the field size for the test a new fixation point is selected at each corner and the test repeated. Each time, the head is repositioned to match being directly in front (height and in line) of the fixation spot.

Macula Integrity Test 534

Figure 14:
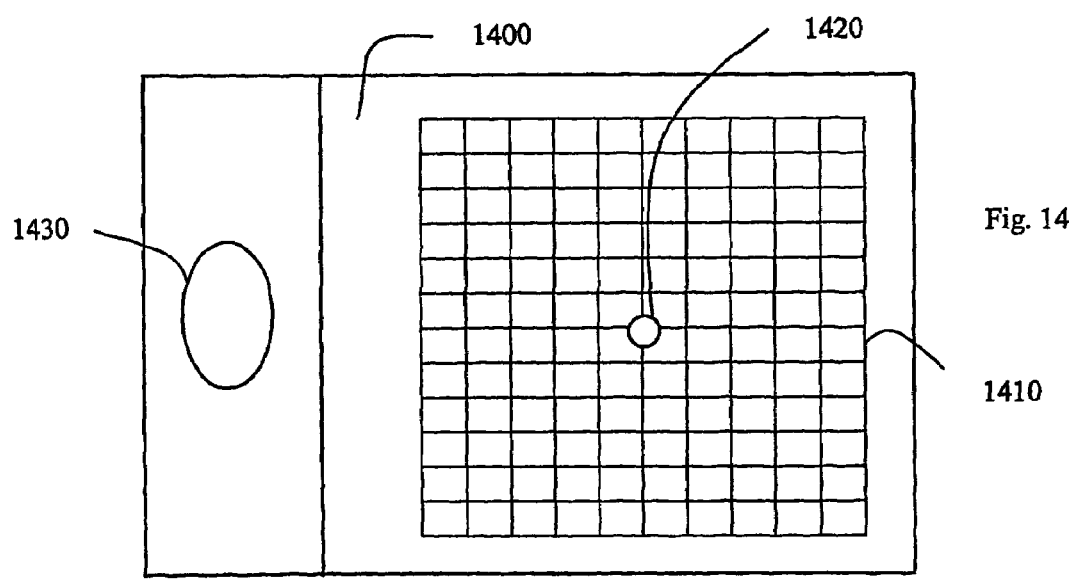
FIG. 14 shows an image used in assessing macula integrity.

The purpose of this test is to determine the integrity of the macula and to record if any changes or deteriorations are occurring. The test 534 makes use of a pattern of white lines 1410 arranged in a square grid on a black background 1400 as shown in FIG. 14. A red fixation spot 1420 is drawn in the center of the grid 1410. A white oval object 1430, flickering at a rate of 3 Hz, is positioned to either or the right or left side of the grid pattern depending on which eye is being tested.

If the patient normally wears visual aids such as glasses or contact lenses they should be used during the test.

The patient is instructed to look at this central red dot 1420 during the test procedure. While fixating on this target object 1420, the patient is to adjust his or her distance from the video display 1914 by rocking backwards or forwards on his or her elbow until the white flickering oval 1430 on the right side disappears into the eye's blind spot. The patient's eyes should also be at the same height as the red dot target object 1420.

By repeatedly drawing the focus of attention to the center of the grid pattern 1410, a more stable mapping of any irregularities may be achieved.

The test 534 is standardized by making use of the patient's blind spot. The vertical oval 1430 is located to the right of the grid pattern 1410 when testing the right eye, and the similar vertical oval 1430 is positioned to the left of the grid pattern 1410 when the left eye is being tested. The size of this vertical oval 1430 is set to be slightly smaller than the blind spot at a working distance of between 25 and 30 cm from the video display 1914. The patient is instructed to cover his or her left eye, and then, while focusing attention on the central red dot 1420, to move his or her head towards or away from the video display 1914 until the white vertical oval 1430 on the right side of the grid 1410 disappears into the blind spot. This should occur when the eye is about 25 to 30 cm from the video display 1914. Once this positioning is achieved, the patient is instructed to note any fading out of the lines or squares in the grid 1410, any distortions of the lines or squares in the grid 1410, and any gaps or incomplete lines or squares. The mouse 1903 is then used to click over the area where any observed distortions appear.

The procedure is then repeated with the right eye covered.

If any distortions of the grid 1410 have been noticed, the patient is requested to contact a local eye care practitioner immediately.

A graphical map is recorded showing any noted distortions. The size and location of the noted distortions provide an indication of the severity of any changes which have occurred to the macula.

Saccades Test 528

Three visual performance tests are provided in order to evaluate a child's ability to fixate, refixate and visually scan characters presented on a flat video display 1914. Each of the three tests examines a different scanning function used in gathering information during the reading process. The tests 528 need to be carried out with the assistance of a supervising adult. In each case the child is given a set task, and the program will then record the time taken to complete the task, and the numbers of errors made. The child's results are cross-correlated with tabulated data relating to expected performance versus age. The result of this operation gives an indication as to how the child's vision may be affecting his or her academic performance.

The first test checks the accuracy with which a child can adjust fixation from a first point to a second point which has a random separation, but following the conventional sequence used in western scripts in which text flows from left to right and top to bottom.

A block of numbers 1500 is presented in the middle of the video display 1914 with an irregular spacing between the numbers, as shown in the example of FIG. 15A. The object of the test is for the child to read all the numbers in the block 1500 as quickly as possible using their eyes only; i.e. the child is not allowed to point with his or her fingers to search and find numbers. A series of 50 numbers is presented. The supervising adult selects a Start and Stop button using the mouse 1903 and notes the numbers of errors made by the child.

The second saccades test looks at the child's ability to scan and identify an image, retain it in memory, and simultaneously count objects and add them to a mental tally.

A block of numbers 1510 is presented in the middle of the video display 1914 consisting of a matrix with ten rows and seven columns, as seen in FIG. 15B. The child is instructed to count how many instances of a particular number are present in the entire block of numbers 1510.

The supervising adult will again select Start and Stop button icons to record the beginning and end of the test, and will record the tally counted by the child. The test is presented four times with four different number searches. For example the child could be asked to count how many times the number "five" appears in the block of numbers 1510 on the video display 1914.

The time taken to complete the test is recorded and also how successful the child was at identifying all the numbers present in the block of numbers 1510.

The third saccades test is a visual-verbal task which tests the child's peripheral visual location and verbal identification skills. The numbers 1 to 20 are displayed on the video display 1914 in a random sequence determined by the computer program. Next to each of the displayed numbers, a randomly chosen letter from the alphabet is displayed. An example of this viewing object 1520 is shown in FIG. 15C. During the test, the child has to locate each number sequentially starting with 1. As the number is located, the child has to call out the number and the associated letter. The supervising adult selects a Start button to begin the test and a Stop button once it is ended. The adult also needs to record the child's performance in the test, with respect to whether the numbers were located in the correct sequence, and whether any letters or numbers were misread. The child has to perform this task using the eyes only, without pointing with his or her fingers to help identify the characters. The helper is also asked to identify whether there was a lot of head movement during the performance of the test.

At the end of the three tests 528, the program provides a report showing the levels achieved by the child in each test and how they rate compared with tabulated age-related data. If a child fails to reach an adequate level for his or her age, the program will display a message on the video display 1914 to the effect that the child's vision may be affecting academic performance and recommending that the child be given vision therapy to counteract the weaknesses.

Color Vision Test 538

There are two purposes to testing color vision. The first is to determine if a patient has difficulty discriminating colors which could affect the patient's daily life. Examples of tasks where color discrimination is required are the identification of electronic components, and the identification of colored signals by pilots, train drivers, etc. The second purpose of testing color vision is to identify deficiencies which are due to disease such as glaucoma or diseases of the optic nerve.

The actual test implemented can be a pre-tested and standardized color vision test used with the permission of the copyright owner. The pre-tested and standardized color vision test is adapted to run as a test 538 on the flat video display 1914, and to provide an automatic recording system in order that untrained users can carry out the test 538. The results are recorded in a computer memory, and are automatically analyzed, calibrated and scaled by the computer software.

Dynamic Tests 318

The following series of tests is designed to assess the binocular status of the patient. In other words the purpose is to determine that the two eyes are working together. The tests assess whether the patient has an accurate binocular fixation (no eye muscle imbalances and/or suppression). They also test the patient's fusion skills and depth perception.

In order to run these tests it is necessary to present a distinct image to either eye. This is achieved by using goggles which have different-colored filters for either eye, or alternatively have liquid crystal display (LCD) filters which are polarized differently for each eye. When different-colored filters are used, one lens will be red and the other will be green or blue. It is necessary that the patient obtain a suitable pair of goggles before the test can be done. The colored filter goggles can be obtained from AiVision Pty Ltd, Sydney, Australia (www.aivision.com.au), over the World Wide Web 202.

Binocular Vision Test Suppression Test 540

In the test 540, six objects (three paired sizes) are displayed on the video display 1914 simultaneously. The objects are colored in such a way that a patient wearing the goggles described above would only see three objects with either eye. Thus, if one eye were to be covered, the user would only see three objects. If the other eye were covered, the other three objects would be seen. The purpose of the test is to view the video display 1914 with both eyes open and to note how many objects can be seen simultaneously and the degree of suppression.

The patient is asked using the mouse to click over each of the shapes that they see on the video monitor. The results are automatically recorded, analyzed and calibrated by the program on the computer.

If only three or two similar-shaped objects are seen then the patient is only using one eye and thus cannot appreciate true three-dimensional vision. If a combination of the shapes is seen it denotes there is some level of simultaneous binocular vision present. If the smaller central images are left out it denotes small central suppression or a fine binocular imbalance.

The test 540 is conducted with the eyes positioned 40 cm from the video display 1914 while wearing the red and green/blue goggles (with the red filters in front of the left eye).

If the patient reports an incorrect response, in which only three or two similar-shaped objects are seen, then no further dynamic testing is performed. A message will be displayed on the video display 1914 advising the patient to consult the nearest practitioner.

Binocular Vision Test 2: Phoria 542

Figure 16:
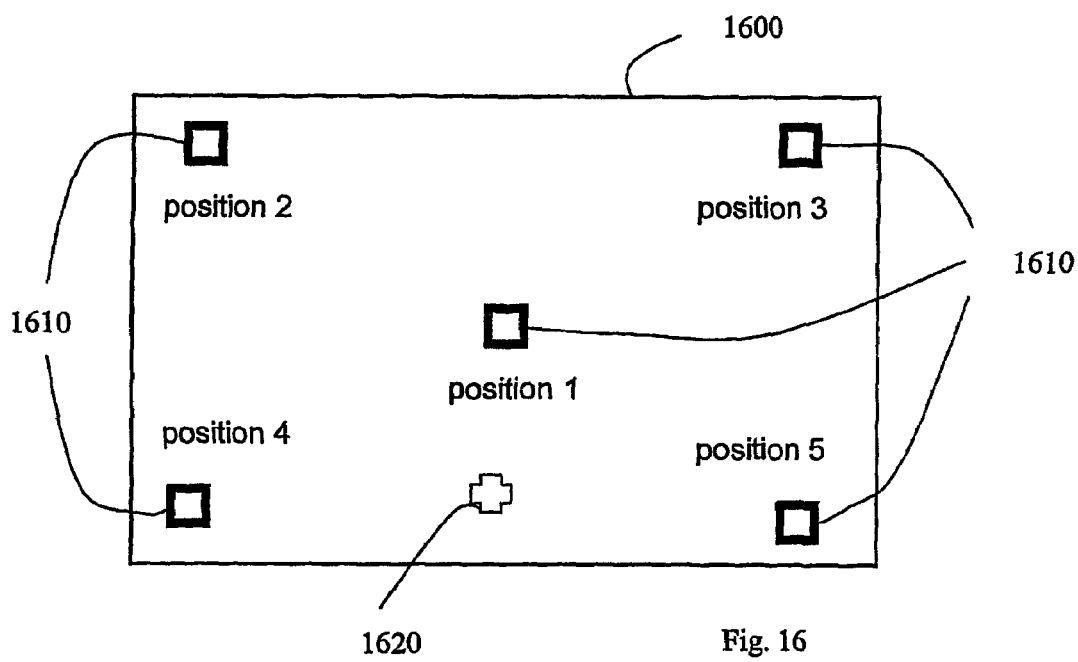
FIG. 16 shows visual objects used in assessing a patient's binocular vision.

The purpose of the phoria test 542 is to determine how well the two eyes are aligned. The test 542 presents five red square objects 1610, four of which are positioned at the corners of the screen 1600 while the fifth square 1610 is positioned at the center as seen in FIG. 16. While the patient is wearing the colored goggles, these red square objects 1610 will only be visible to one eye. A green cross-shaped object 1620 is also displayed, which is only visible to the other eye.

The patient is instructed to position his or her head 40 cm from the video display 1914 while wearing the colored goggles. The object is then to move the green cross-shaped object 1620 using the mouse 1903 and to position it inside each of the five red square objects 1610 in turn. Once the patient perceives the cross to be inside a square 1610, the left mouse button is clicked to record the perceived position. The procedure is continued until the patient has attempted to position the green cross 1620 in each of the five red squares 1610.

The test 542 records the disparity between the true and the perceived positions of the two objects in each of the five locations. Any disparity between the real and perceived location of the two objects will indicate a muscle imbalance, i.e. whether the eyes under-converge, over-converge or have a vertical imbalance. Any misalignment is an indication of the ocular posturing of the eyes during the state of rest.

Binocular Vision Test 3: Fusion 544

Figure 17:
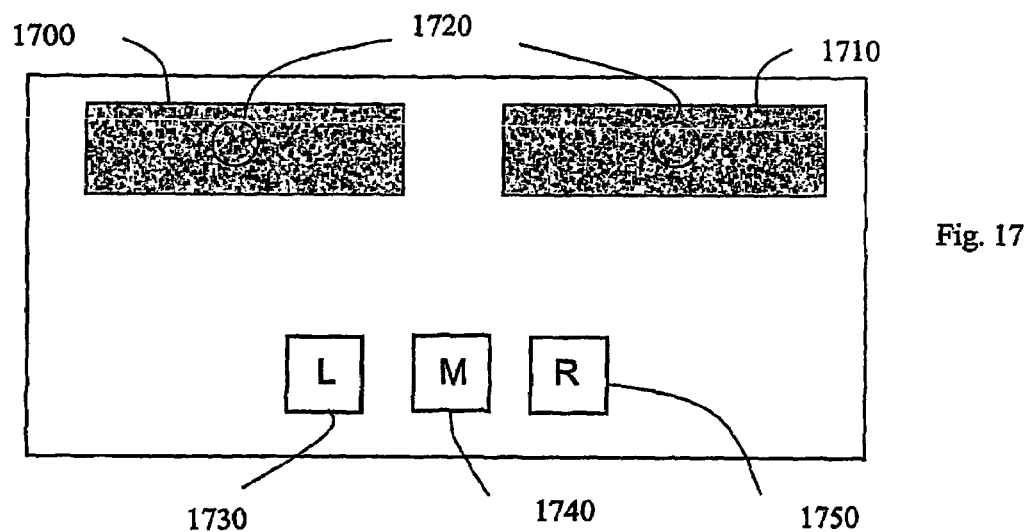
FIG. 17 shows objects used in assessing a patient's ability to fuse images.

The purpose of the fusion test 544 is to test the visual system's ability to fuse two images into a single image. The test 544 makes use of two rectangles 1700, 1710 of identical size as seen in FIG. 17. The first rectangle 1700 has a speckled red background, and is only visible to the eye associated with the red filter of the goggles. The second rectangle 1710 has a green or blue speckled background, and is hence visible only to the other eye.

At the start of the test the two rectangles 1700, 1710 are overlayed to appear as one image. A red and green/blue random dot stereogram of a circle 1720 is displayed on the video display 1914 such that it will appear within the overlayed rectangles 1700, 1710 in one of three locations, namely to the left of the rectangle, in the middle, or to the right of the rectangle. By selecting one of three buttons 1730, 1740, 1750 on the video display 1914 using the mouse 1903, the patient is able to identify the location of the circle 1720 within the rectangle.

In the first part of the test 544 the red-colored rectangle 1700 is moved to the right. Once again the patient is asked to identify the location of the circle 1720 within the perceived rectangle. This tests the ability of the brain to hold the two images together. If the location is correctly identified, the red colored rectangle 1700 is moved further to the right. This process is repeated until the break of convergence fusion is reached. At this point the patient will not be able to identify where the circle 1720 is located in the rectangle.

In the second part of the test the procedure is the same except that the red rectangle 1700 is moved to the left from the overlapping start position. The point at which the patient can no longer identify the location of the circle 1720 within the perceived rectangle identifies the divergence fusion demand.

The maximum separation in each direction relates to the fusion or range for both divergence and convergence. The results are recorded and automatically analyzed, calibrated and scaled by the computer program stored in the computer 1901. The results are recorded in dioptric values (prism diopters disparity).

Binocular Vision Test No. 4: Stereopsis 546

This test 546 is similar to the fusion test 544, but instead of moving the background rectangle 1700, the stereoscopic information defining the circle 1720 is varied. The purpose of the test 546 is to click on one of three boxes 1730, 1740, 1750 on the screen marked "L" "M" "R" respectively as seen in FIG. 18, in order to indicate whether the circle 1720 is perceived to be located to the left, in the middle or to the right of the background rectangle 1800. If a correct response is given the stereoscopic demand is increased until the patient is unable to tell where the circle 1720 is located within the background rectangle 1800.

The test 546 is conducted with the eyes 40 cm from the video display 1914 while wearing the red and green/blue goggles (the red filter in front of the left eye).

A rectangle 1700, 1710 with either a red or a green/blue speckled background is presented individually to each eye. A circular stereo target 1720 is randomly superimposed in any one of three locations within the background rectangle 1800 as shown in FIG. 18.

The test 546 is repeated up to a further four times using rectangles 1700, 1710 containing circles 1720 where the depth disparity becomes more acute.

The results are automatically recorded, analyzed and calibrated by the program on the computer 1901 in seconds of arc.

It will be appreciated from the above that the various visual tests, with the exception of the test set-up (calibration), although described in a certain order, need not be performed in any particular order, or need all be performed, depending upon the type of examination that is desired. Typically, however, the application program, once enabled for patient testing, will take the patient through the various tests in a step-by-step, test-by-test fashion until optical examination is complete and a thorough evaluation of the test data can then be performed.

Diagnostic Assistant Program

When the series of static and dynamic visual tests 316, 318 has been completed, the patient responses representing the results of the tests 316, 318 are encrypted by the active document installed on the patient's local computer 1901. The encrypted results are then sent back via the World Wide Web 202 to the host computer system 214, where the results are decrypted and analyzed, ideally by a legally registered optometrist trained in the use of the program and tests, who is able to formulate and give professional advice on corrective lens prescriptions or recommendations regarding further treatment. The recommendations may be returned to the patient by e-mail 232 or by regular mail.

In an alternative approach, the diagnosis may be performed by a diagnostic assistant program 700. This is a computer program which uses artificial intelligence technology including logic code and artificial neural networks in order to mirror the way a trained optometrist would analyze the optometric data obtained from clinical testing of the patient's visual functioning. In the first instance the clinical validation 224 can screen the results of the remote testing in order to ensure reliability and consistency of the test results. The diagnostic assistant program 700 can then calculate a suitable lens prescription in order to correct the patient's refractive condition using an artificial intelligence/logic sequence described below. This analysis could be based either on the results of the flat-screen testing described earlier, or alternatively could be based on standard clinical optometric tests. In the latter case the data from the tests would have to be captured in a computer readable format.

The use of the diagnostic assistant program can speed up the lens prescription process considerably, and further provides a standard objective reference in analyzing visual functions.

Figure 7:
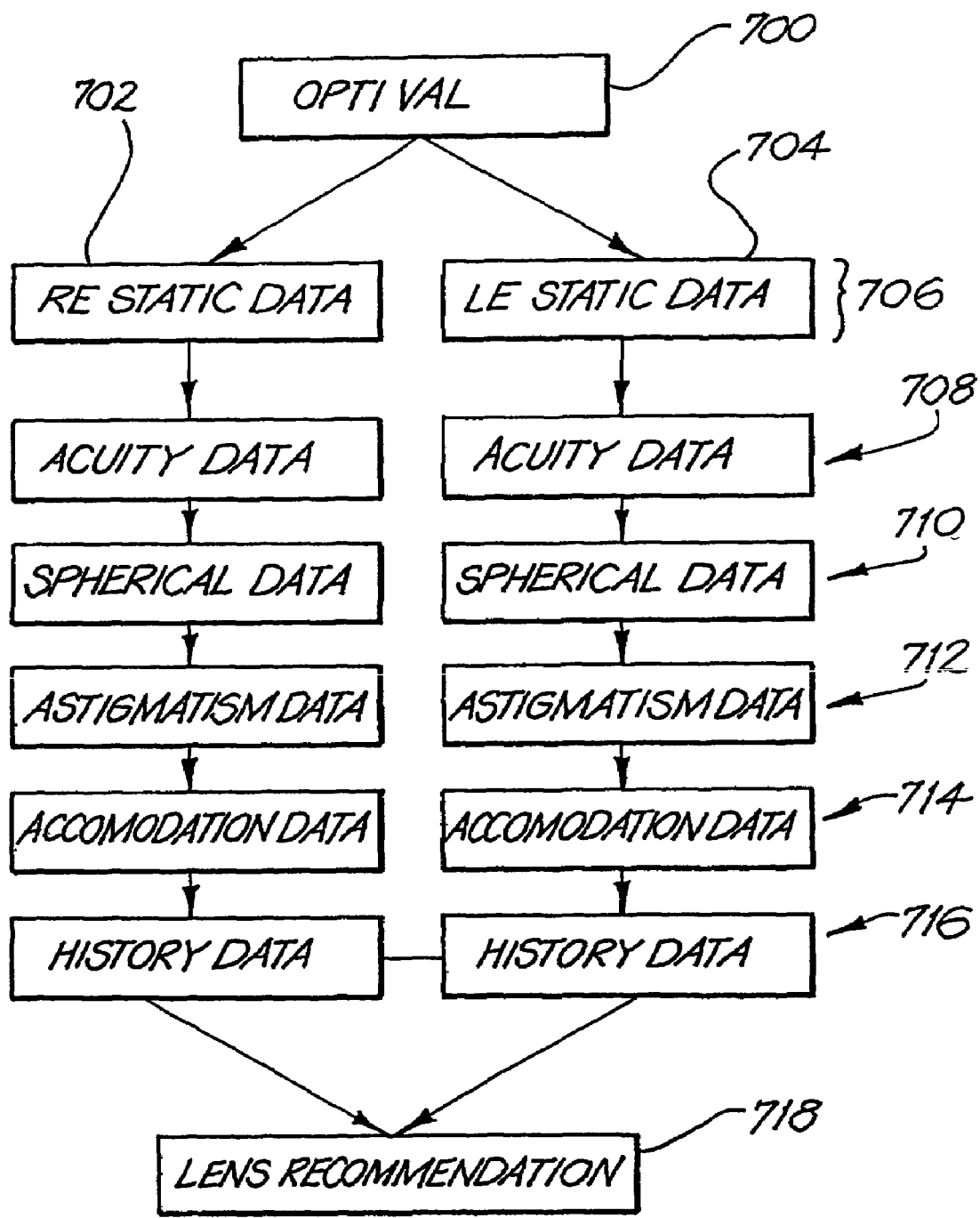
FIG. 7 shows a schematic data flow diagram illustrating the analysis of optical layer problems by a diagnostic assistant program.

FIG. 7 illustrates the data flow through the diagnostic assistant program 700 (named OptiVal) during the analysis relating to the optical layer 100. The diagnostic assistant program 700 is composed of a large number of logical equations organized in modules which represent different parts of the visual analysis process. Each module interacts with other modules in order to provide an analytical chain which has been adjusted experimentally to give suitable recommendations for lens prescriptions. The supervisory module 700 first considers the data 702 relating to the static tests of the right eye, and data 704 relating to static data for the left eye. The analysis then proceeds to acuity data 708 gathered during the tests 314, 316, 318 for either eye. Thereafter the spherical data 710 is considered, followed by an analysis of the astigmatism data 712, and the accommodation data 714. Finally, the diagnostic assistant program considers the history data 716 which the patient provided when answering the questionnaire 518.

The diagnostic assistant program, simulating the reasoning of a trained optometrist, will then produce a lens recommendation 718.

The diagnostic assistant program can also analyze the results of the visual testing in order to identify the severity of the visual disorders at all three layers of the visual process 100, 102, 106

Figure 8:
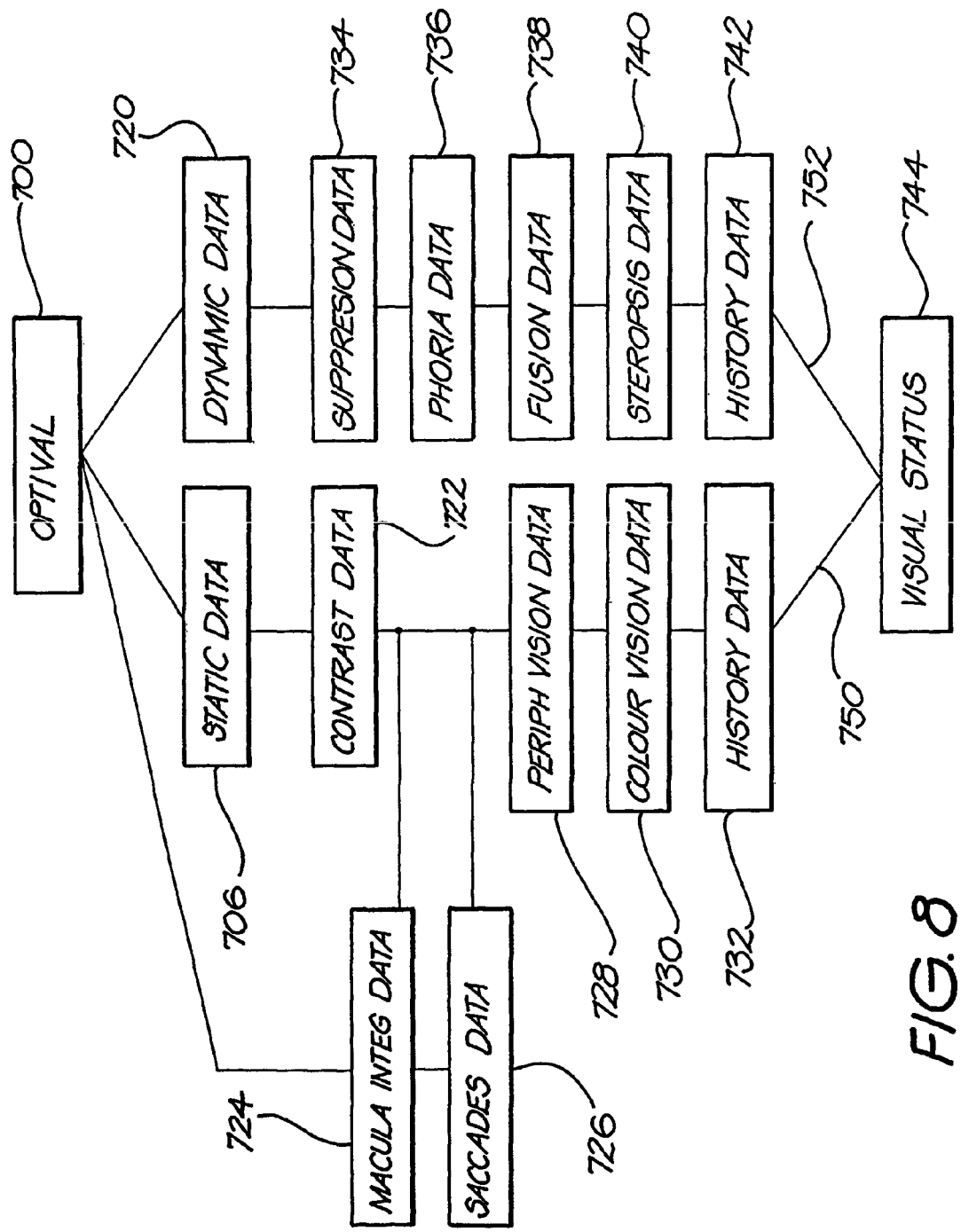
FIG. 8 shows a schematic data flow diagram illustrating how the diagnostic assistant program analyzes data concerning the functional and perceptual layers.

FIG. 8 shows a data flow diagram illustrating how the diagnostic assistant program analyzes the test data to assess what problems occur in the functional layer 102 and the perceptual layer 106. The program is composed of a large number of logical equations organized in modules. The analysis process mirrors that which would be carried out by a trained optometrist. The supervisory module 700 first examines data 706 associated with static testing. The results of this analysis are considered when analyzing data 722 associated with contrast testing. The supervisory program 700 also initiates an analysis of the data 724 stored during the testing of macular integrity, or in the case where the patient is a child, saccades data 726. The inferences drawn from the analysis of data 724 and 726 are combined with the analysis of static data 706 and contrast data 722 before analyzing data 728 associated with peripheral vision tests. Building on this analysis, the dynamic assistant program proceeds to analyze data 730 associated with the color vision test, and then reviews the conclusions reached in the light of history data 732 collected from the patient when answering the questionnaire 518. The analysis of data 706, 722, 724, 726, 728, 730 and 732 leads to a first set of conclusions 750.

In a separate data flow path, the supervising module 700 initiates an analysis of data 720 derived from dynamic tests. The analysis will then in sequence address the suppression data 734, the phoria data 736, the fusion data 738, the stereopsis data 740 and history data 742 in order to reach a second set of conclusions 752. The diagnostic assistant program then combines the first set of conclusions 750 with the second set of conclusions 752 in order to produce an assessment of the patient's visual status 744.

The vision care professional is presented with the data, the outcome of the analytical process, and comparisons with other patients' cases which can then be used as the basis for their clinical decisions.

In many jurisdictions there will be laws which specify that the diagnostic analysis of vision problems (the optical layer 100) must be carried out by a licensed optometrist, ophthalmologist or other person as described in the various statutes. Therapy involving drug treatment (required for problems in the functional layer 102 and perceptual layer 106) may only be carried out by a registered medical practitioner.

The optometrist, who will have access to a large database 226 of clinical results from previous tests, will examine all the results and reach a conclusion which will then be forwarded to the patient.

If the optometrist believes that there are no problems involving the functional or perceptual layer 106 and the diagnosis is likely to be reliable, the optometrist may issue a prescription for glasses where required to correct optical layer problems. The optometrist may also issue information about eye exercises.

If the test results are inconsistent or indicate possible problems with the functional laser 102 or perceptual layer 106, the patient will be advised to see an appropriate professional eye care specialist in their own locality.

An important aspect of the lensless flat-screen vision testing system described herein is mobility. To obtain mobility at realistic costs it is necessary to separate the eye test measurements from the professional vision diagnosis.

When this lensless flat-screen vision testing system is disseminated by a network such as the World Wide Web 202, the new vision analysis system allows the vision testing to be carried out remotely in several ways.

Where there is access to a computer 1901 connected to the Web 202, individual patients from anywhere in the world may run the tests by logging onto a web page 300, thereby freeing themselves from the need to travel and attend a clinic. Where the patients are not fully capable of running the tests by themselves, as a result of disability, age, language or any other problem, they may be assisted by people without optometric training.

The vision system may alternatively or additionally be used in small shops or booths as a franchise style of operation. The system can also enable individual optometrists to set up low-overhead computer-based optometry clinics where the test equipment is rented or leased.

Where there is no computer access, people without optometric training can take lightweight portable computers, such as notebook computers, palm computers, combined with the new thin-form lightweight monitors, to patients. These mobile test stations can connect to the Web 202 either directly by a wired connection or remotely via a cellular telephone or satellite telephone connection or other available media. A mobile self-contained unit can provide full diagnostic capabilities, when operated by people with optometric training, as on-the-spot professional decisions may be required.

A supervising optometrist located at a base station can supervise, via computer, a number of mobile Vision Service Technicians (VST). The VSTs can visit patients at preferred locations (for example home, office, hospital) and carry out the vision measurement testing using a similar set of tests as available on the network version of the program.

On arrival at the patient's location, the VST can link via computer or cellular telephone to the base station and conduct the vision testing session. The results of each test may be fed back to the base station on completion.

The supervising optometrist can thus watch the progress of the tests, answer any questions, request further information and at the end of the test forward a diagnosis to the VST for action.

Since the VST is present at the vision test, he or she will also be able to carry out a simple examination of the patient's eyes for possible functional layer problems and report back to the optometrist at the base station either by sending an image of the findings or a report on the observations of any irregularities observed.

The lensless flat-screen vision testing technology may also be disseminated by the use of franchise operations. The lensless flat-screen vision testing methodology means that routine vision testing may be carried out using little more than a personal computer and an Internet connection. This suggests the establishment of a new low-cost vision test center where several people could be tested simultaneously by a single optometrist.

The invention claimed is:

1. A computer-implemented method for testing vision of a human subject, said method comprising the steps of:
   (a) adjusting at least one setting of a display device such that a sequence of graphic objects displayed on said display device conforms to a pre-defined appearance;
   (b) displaying said sequence of graphic objects on said display device to perform series of tests of the visual functioning of the human subject;
   (c) recording actions of the human subject performed in response to the display of said sequence of graphic objects;
   (d) calculating from said recorded actions at least one aspect of the visual functioning of the subject; and
   (e) calculating at least one corrective lens prescription for the human subject from at least one of the calculated aspects of the visual functioning of the subject.

2. A method as claimed in claim 1, the method comprising the further step of:
   (f) notifying said sequence of graphic objects based on said at least one action of the human subject.

3. A method as claimed in claim 1, wherein each said graphic object relates to at least one visual test of a set of visual tests able to be performed, and an order in which said tests are performed is varied such that at least one following test is selected from said set based on a response of the human subject to a current one of said tests.

4. A method as claimed in claim 1, wherein step (a) comprises the sub-steps of:
   (aa) loading computer executable instructions into a memory means of a computer connected to said display device;
   (ab) running a first portion of said computer executable instructions to adjust the black and white contrast of said display device to match a predetermined black and white contrast; and
   (ac) running a second portion of said computer executable instructions to adjust the intensity of at least one color used in the display of color images on said display device such that said at least one color contained in images displayed on said display device conforms to a corresponding pre-defined color.

5. A method as claimed in claim 1, wherein a first test of the series of tests of step (b) comprises the sub-steps of:
   (ba) displaying a first visual object on said display device such that said first visual object increases in size in the range from a predetermined minimum size to a predetermined maximum size;
   (bb) halting the growth of said first visual object as soon as the human subject, viewing said first visual object from a predetermined distance, is able to distinguish a feature of said first visual object; and step (c) comprises the sub-step of:
   (ca) recording the size of said first visual object when the growth of said first visual object was halted.

6. A method according to claim 5, wherein said predetermined minimum size is 2 mm high and said predetermined maximum size is 150 mm high.

7. A method as claimed in claim 5, wherein said first visual object comprises a plurality of black E-shaped characters against a white background.

8. A method as claimed in claim 7, wherein said visual objects are displayed on a red colored background.

9. A method as claimed in claim 8, wherein straight lines are arranged radially around a central region and said straight lines are rotated.

10. A method as claimed in claim 7, wherein said visual objects are displayed on a green colored background.

11. A method as claimed in claim 5, wherein said first visual object comprises a plurality of black C-shaped objects, each of said C-shaped characters being enclosed within a black border.

12. A method as claimed in claim 1, wherein a second test of the series of tests of step (b) comprises the further step of:
- (bd) displaying sets of straight lines on said display device, said lines being rotated from the vertical by angles ranging between 0° and 360°; step (c) comprises the step of:
- (cb) selecting those of said lines perceived by the human subject to be darker; and step (d) comprises the step of:
- (da) calculating an astigmatism of the human subject from said selected lines.

13. A method as claimed in claim 12, wherein said straight lines are arranged in a fan shape.

14. A method as claimed in claim 12, wherein said straight lines are grouped in a plurality of squares with each line within each said square being substantially parallel to the other lines within said square, the lines for adjacent ones of said squares being inclined to each other.

15. A method as claimed in claim 1, wherein a third test of the series of tests of step (b) comprises the sub-steps of:
- (be) initializing a first visual object comprising parallel lines having a first spatial frequency and being rotated from the vertical by an angle between 0° and 360°;
- (bf) displaying said first visual object on said display device such that a spatial frequency of said parallel lines is progressively decreased from said first spatial frequency;
- (bg) halting sub-step (bf) when the human subject, viewing said first visual object from a predetermined distance, is able to distinguish a feature of said first visual object; and step (c) comprises:
- (cc) recording the spatial frequency of said parallel lines when step (bf) is halted.

16. A method as claimed in claim 15, wherein said first visual object is taken from the group consisting of a grey-scale pattern, a red-scale pattern and a blue-scale pattern.

17. A method as claimed in claim 15, wherein step (d) comprises the sub-steps of:
- (db) calculating a visual acuity of the human subject; and
- (dc) from said visual acuity, calculating aspects of spherical and cylindrical lens prescription components for the human subject.

18. A method as claimed in claim 1, wherein a fourth test of the series of tests of step (b) comprises the sub-steps of:
- (bh) initializing at least one visual object at a first contrast level, said at least one visual object having a cyclically varying parameter and being rotated from the vertical by an angle between 0° and 360°;
- (bi) displaying said first visual object on said display device such that a contrast level of said at least one visual object is progressively increased from said first contrast level;
- (bj) halting sub-step (bi) when the human subject, viewing said first visual object from a predetermined distance, is able to distinguish a feature of said first visual object; and step (c) comprises:
- (cd) recording the contrast level of said at least one visual object when step (bi) is halted.

19. A method as claimed in claim 1, wherein a fifth test of the series of tests of step (b) comprises the sub-steps of:
- (bk) displaying a fixation object and a positioning object such that said positioning object is in a blind spot of the human subject's vision when the human subject fixates on said fixation object from a predetermined distance from said display device;
- (bl) displaying a moving object and a pointer object while the human subject views said display device from said predetermined distance, said pointer object being controllable by the human subject to overlay said moving object; and
- (bm) intermittently displaying a peripheral object while the human subject controls said pointer object;

step (c) comprises the sub-step of:
- (ce) recording a response of the human subject if the human subject correctly observes said peripheral object while correctly positioning said pointer object over said moving object; and step (d) comprises the sub-step of:
- (dd) calculating a measure of said subject's peripheral vision from said response.

20. A method as claimed in claim 1, wherein a sixth test of the series of tests of step (b) comprises the sub-steps of:
- (bn) displaying a fixation object and a positioning object such that said positioning object is in a blind spot of said subject's vision when the human subject fixates on said fixation object from a predetermined distance from said display device; and
- (bo) displaying a grid object associated with at least said fixation object;

step (c) comprises the sub-step of:
- (cf) recording any irregularities in said grid object perceived by the human subject when said subject views said grid object from said predetermined distance and the human subject fixates on said fixation object; and step (d) comprises the sub-step of:
- (de) calculating a measure of said subject's macula integrity from said recorded irregularities.

21. A method as claimed in claim 1, wherein a seventh test of the series of tests of step (b) comprises the sub-steps of:
- (bp) displaying a series of objects spaced at irregular intervals and requesting the human subject to identify said objects; and step (c) comprises the sub-step of:
- (cg) recording a number of correct identifications and a total time taken by the human subject to identify said objects.

22. A method as claimed in claim 21, wherein step (d) comprises the sub-steps of:
- (df) evaluating from step (c) an ability of the human subject to fixate, refixate and visually scan objects;
- (dg) comparing said ability with statistical data relating expected ability to age.

23. A method as claimed in claim 1, wherein an eighth test of the series of tests of step (b) comprises the sub-step of:
- (bq) displaying a series of objects and requesting said subject to identify those of said objects that are substantially identical; and step (c) comprises the sub-step of:
- (ch) recording a number of correct identifications and a total time taken by said subject to identify said objects.

24. A method as claimed in claim 1, wherein a ninth test of the series of tests of step (b) comprises the sub-step of:
- (br) displaying a sequence of numbers in a random order, each of said numbers having an associated letter, and requesting the human subject to locate said numbers in a prescribed order and to identify the associated letters; and step (c) comprises the sub-step of:
  (ci) recording a number of correct locations and identifications and a total time taken by the human subject to locate and identify said sequence.

25. A method as claimed in claim 1, wherein a tenth test of the series of tests of step (b) comprises the sub-steps of:
  (bs) placing a first filter between a first eye of the human subject and said display device and a second filter between a second eye of the human subject and said display device; and
  (bt) displaying a first set of objects visible through said first filter but not visible through said second filter, and a second set of objects visible through said second filter but not visible through said first filter;
  step (c) comprises the sub-step of:
  (cj) recording a total number of objects seen by the human subject when viewing said display device with both eyes simultaneously; and
  step (d) comprises the sub-step of:
  (dh) calculating a measure of binocular vision of the human subject from said total number.

26. A method as claimed in claim 1, wherein an eleventh test of the series of tests of step (b) comprises the sub-steps of:
  (bu) placing a first filter between a first eye of the human subject and said display device and a second filter between a second eye of the human subject and said display device; and
  (bv) displaying a first set of objects visible through said first filter but not visible through said second filter, and at least one moveable object visible through said second filter but not visible through said first filter, said at least one moveable object being controllable by the human subject;
  step (c) comprises the sub-step of:
  (ck) recording whether or not the human subject can align said at least one moveable object with at least one object from said first set of objects; and
  step (d) comprises the sub-step of:
  (di) calculating a measure of alignment between the first eye and the second eye of the human subject.

27. A method as claimed in claim 1, wherein a twelfth test of the series of tests of step (b) comprises the sub-steps of:
  (bw) placing a first filter between a first eye of the human subject and said display device and a second filter between a second eye of the human subject and said display device; and
  (bx) displaying a first object visible through said first filter but not visible through said second filter, and a second object visible through said second filter but not visible through said first filter, such that the human subject viewing said first object and said second object perceives an image having an identifiable location;
  (by) moving said first object away from said second object on said display device until said subject no longer perceives said image;
  step (c) comprises the sub-step of:
  (cl) recording a separation between said first object and said second object when the human subject no longer perceives said image; and
  step (d) comprises the sub-step of:
  (dj) calculating from said separation a measure of the ability of the human subject to fuse images.

28. A method as claimed in claim 1, wherein step (a) comprises the sub-steps of:
  (ad) displaying one or more calibration objects on said display device;
  (ae) comparing a size of said one or more calibration objects with a size of a corresponding physical object;
  (af) adjusting the size of said one or more calibration objects to be substantially the same as the size of the corresponding physical object; and
  (ag) calibrating said display device based on said adjustment.

29. A method as claimed in claim 28, wherein said physical objects are taken from the group consisting of a credit card, a diskette and a 10 cm by 10 cm square.

30. A method as claimed in claim 1, wherein step (a) comprises the sub-steps of:
  (ah) displaying a set of objects having a first color on said display device against a background having a second color differing by less than 5% from said first color; and
  (ai) adjusting at least one source of ambient light if one or more of said set of objects are not visible when said display device is viewed from a pre-defined distance.

31. An apparatus for testing vision in a human subject, the apparatus comprising:
  means for adjusting at least one setting of a computer display such that a sequence of graphic objects displayed on said computer display conforms to a pre-defined appearance;
  means for displaying said sequence of graphic objects on said computer video display for performing a series of tests of the visual functioning of said human subject;
  means for recording actions of said human subject performed in response to the display of said sequence of graphic objects;
  means for calculating from said recorded actions at least one aspect of the visual functioning of said subject; and
  means for calculating at least one corrective lens prescription for the human subject from at least one of the calculated aspects of the visual functioning of the subject.

32. A computer program element comprising computer program code means to make a computer execute a procedure to:
  adjust at least one setting of a video display of said computer such that a sequence of graphic objects displayed on said video display conforms to a pre-defined appearance;
  display said sequence of graphic objects on said video display to perform a series of tests of the visual functioning of said human subject;
  record actions of said human subject performed in response to the display of said sequence of graphic objects;
  calculate from said recorded actions at least one aspect of the visual functioning of said subject; and
  calculate at least one corrective lens prescription for the human subject from at least one of the calculated aspects of the visual functioning of the subject.

33. A computer readable medium, having a program recorded thereon, where the program is configured to make a computer execute a procedure to:
  adjust at least one setting of a video display of said computer such that a sequence of graphic objects displayed on said video display conforms to a pre-defined appearance;
  display said sequence of graphic objects on said video display to perform a series of tests of the visual functioning of said human subject;
  record actions of said human subject performed in response to the display of said sequence of graphic objects;

calculate from said recorded actions at least one aspect of the visual functioning of said subject; and calculate at least one corrective lens prescription for the human subject from at least one of the calculated aspects of the visual functioning of the subject.

34. A system for the testing of vision in a human subject, said system comprising:
   (a) a server having:
   a first memory for storing an application program and one or more test results from visual testing of a human subject;
   means for receiving said one or more test results;
   means for transmitting said application program;
   means for processing said one or more test results to calculate at least one aspect of the visual functioning of the human subject; and
   means for calculating at least one corrective lens prescription for the human subject from said at least one aspect of the visual functioning of the subject; and
   (b) a client computer having:
   a display device for displaying a sequence of graphic objects to the human subject;
   means for receiving said application program;
   means for running said application program to adjust at least one setting of said display device such that said sequence of graphic objects displayed on said display device conforms to a pre-defined appearance;
   means for recording said one or more test results of the human subject in response to the display of said sequence of graphic objects; and
   means for transmitting said one or more test results to said server.

35. A method of standardising the appearance of visual objects displayed on a video display, the method comprising the steps of:
   installing an application program file on a computer;
   displaying said visual objects on said video display connected to said computer;
   requesting a person viewing said video display to confirm the size of at least one of said visual objects;
   requesting the person to confirm whether a specified one of said visual objects is visible; and
   said application program file utilising the responses of the person to said requests to adjust the relative outputs of the colours used in displaying said visual objects and the relative dimensions of said visual objects.

36. A computer-implemented method for measuring the vision of a human subject, said method comprising the steps of:
   displaying on a display device a first test to check whether the vision of said subject is within a measurement range of said method;
   displaying on said display device a second test to determine a required sensitivity of said method;
   selecting, based on responses of said subject to said first and second tests, further tests to display on said display device to measure an optical power of one or both eyes of said subject; wherein said further tests are selected from the group consisting of:
   tests of visual acuity;
   tests of spherical power;
   tests of cylindrical power;
   tests for astigmatism; and
   tests for near visual acuity;
   and wherein said subject views said first test, said second test and said further tests without lenses being interposed between said display device and said subject.

37. A method as claimed in claim 36, comprising the further step of:
   calculating a corrective lens prescription based on responses of said subject to said further tests.

38. A method as claimed in claim 36 wherein said subject views said tests from more than one predetermined test distance from said display device.

39. A method as claimed in claim 36 comprising the further step of:
   displaying on said display device screening tests to check for pathological conditions in the vision of said subject.

40. A method as claimed in claim 36 wherein said further tests form a sequence of tests in which later tests in said sequence are selected based on responses of said subject to earlier tests in said sequence.

* * * * *